US012800588B2

(12) United States Patent
Patel et al.

(10) Patent No.: US 12,800,588 B2
(45) Date of Patent: Nov. 17, 2026

(54) POLYPEPTIDE CAPTURE, IN SITU FRAGMENTATION AND IDENTIFICATION

(71) Applicant: NAUTILUS SUBSIDIARY, INC., Seattle, WA (US)

(72) Inventors: Sujal M. Patel, Seattle, WA (US); Parag Mallick, San Mateo, CA (US)

(73) Assignee: NAUTILUS SUBSIDIARY, INC., Seattle, WA (US)

( * ) Notice: Subject to any disclaimer, the term of this patent is extended or adjusted under 35 U.S.C. 154(b) by 0 days.

(21) Appl. No.: 19/425,228

(22) Filed: Dec. 18, 2025

(65) Prior Publication Data

US 2026/0126449 A1 May 7, 2026

Related U.S. Application Data

(63) Continuation of application No. 18/463,063, filed on Sep. 7, 2023.

(60) Provisional application No. 63/377,249, filed on Sep. 27, 2022.

(51) Int. Cl.
*G01N 33/68* (2006.01)

(52) U.S. Cl.
CPC ..... *G01N 33/6818* (2013.01); *G01N 33/6842* (2013.01); *G01N 2333/95* (2013.01)

(58) Field of Classification Search
CPC ........... G01N 33/6818; G01N 33/6842; G01N 2333/95
See application file for complete search history.

(56) References Cited

U.S. PATENT DOCUMENTS

| | | | |
|---|---|---|---|
| 6,565,727 | B1 | 5/2003 | Shenderov |
| 6,773,566 | B2 | 8/2004 | Shenderov |
| 6,911,132 | B2 | 6/2005 | Pamula et al. |

(Continued)

FOREIGN PATENT DOCUMENTS

| | | |
|---|---|---|
| EP | 1642131 | 10/2008 |
| WO | WO 2005/010145 | 2/2005 |

(Continued)

OTHER PUBLICATIONS

Egertson et al., "A theoretical framework for proteome-scale single-molecule protein identification using multi-affinity protein binding reagents", BioRxiv (2021), DOI: 10.1101/2021.10-11.463967.

(Continued)

*Primary Examiner* — Robert B Mondesi
*Assistant Examiner* — Dalton Edward Kiefer
(74) *Attorney, Agent, or Firm* — Knobbe, Martens, Olson & Bear LLP

(57) ABSTRACT

The present disclosure provides a method of identifying a polypeptide. The method can include steps of (a) attaching a polypeptide to a particle or solid support, thereby producing an immobilized polypeptide having a plurality of amino acids linked to the particle or solid support; (b) fragmenting the immobilized polypeptide, whereby the particle is attached to a set of fragments of the polypeptide; (c) performing a binding assay including contacting the set of fragments with a plurality of affinity reagents and detecting binding of affinity reagents of the plurality of affinity reagents to the set of fragments; and (d) identifying the polypeptide from results of the binding assay.

19 Claims, 6 Drawing Sheets

(56) References Cited

U.S. PATENT DOCUMENTS

| | | | |
|---|---|---|---|
| 6,977,033 | B2 | 12/2005 | Becker et al. |
| 7,052,244 | B2 | 5/2006 | Fouillet et al. |
| 7,252,954 | B2 | 8/2007 | Wang et al. |
| 7,547,380 | B2 | 6/2009 | Velev |
| 7,641,779 | B2 | 1/2010 | Becker et al. |
| 8,501,923 | B2 | 8/2013 | Rothemund |
| 9,340,416 | B2 | 5/2016 | Maune et al. |
| 9,528,984 | B2 | 12/2016 | Mitra |
| 10,473,654 | B1 | 11/2019 | Mallick |
| 11,203,612 | B2 | 12/2021 | Gremyachinskiy et al. |
| 11,282,585 | B2 | 3/2022 | Patel et al. |
| 11,505,796 | B2 | 11/2022 | Aksel et al. |
| 11,692,217 | B2 | 7/2023 | Aksel et al. |
| 2005/0026215 | A1 | 2/2005 | Predki et al. |
| 2005/0042648 | A1 | 2/2005 | Griffiths et al. |
| 2005/0079510 | A1 | 4/2005 | Berka et al. |
| 2005/0130173 | A1 | 6/2005 | Leamon et al. |
| 2020/0082914 | A1 | 3/2020 | Patel et al. |
| 2020/0318101 | A1 | 10/2020 | Mallick et al. |
| 2020/0319200 | A1 | 10/2020 | Havranek et al. |
| 2020/0348307 | A1 | 11/2020 | Beierle et al. |
| 2021/0239705 | A1 | 8/2021 | Mallick |
| 2021/0390705 | A1 | 12/2021 | Egertson et al. |
| 2022/0050049 | A1 | 2/2022 | Indermuhle et al. |
| 2022/0227890 | A1 | 7/2022 | Kapp et al. |
| 2022/0236282 | A1 | 7/2022 | Mallick et al. |
| 2022/0379582 | A1 | 12/2022 | Sorelle et al. |
| 2022/0412998 | A1 | 12/2022 | Lobanov et al. |
| 2023/0090454 | A1 | 3/2023 | Kapp et al. |
| 2023/0114905 | A1 | 4/2023 | Egertson et al. |
| 2023/0149883 | A1 | 5/2023 | Indermuhle et al. |
| 2023/0167488 | A1 | 6/2023 | Robinson et al. |
| 2023/0287480 | A1 | 9/2023 | Stern et al. |
| 2023/0314324 | A1 | 10/2023 | Jouzi et al. |
| 2023/0360732 | A1 | 11/2023 | Egertson et al. |
| 2024/0133892 | A1 | 4/2024 | Patel et al. |

FOREIGN PATENT DOCUMENTS

| | | | |
|---|---|---|---|
| WO | WO2019195633 A1 * | 10/2019 | |
| WO | WO2019236749 A2 * | 12/2019 | |
| WO | WO 2020/106889 | 5/2020 | |
| WO | WO 2023/122589 | 6/2023 | |
| WO | WO 2024/072614 | 4/2024 | |

OTHER PUBLICATIONS

Howard et al., "Solid-phase peptide capture and release for bulk and single-molecule proteomics", ACS Chemical Biology, vol. 15(6):1401-1407 (2020).

Okano et al., "Thermally on-off switching polymers for durg permeation and release", Journal of Controlled Release, vol. 11(1-3):255-265 (1990).

Rothemund et al., "Folding DNA to create nanoscale shapes and patterns", Nature, vol. 440(7082):297-302 (2006).

Schild, "Poly(N-Isopropylacrylamide): Experiment, theory and application", Progress in Polymer Science, vol. 17(2):163-249 (1992).

Sigl et al., "Programmable icosahedral shell system for virus trapping", Nat Mater, vol. 20(9):1281-1289 (2021).

Xu et al., "Photoresponsive supramolecular polymers: From light-controlled small molecules to smart materials", Adv. Mater, vol. 35:2204413 (2023).

Zakeri et al., "Peptide tag forming a rapid covalent bond to a protein, through engineering a bacterial adhesin", Proceedings Natl. Acad. Sciences USA, vol. 109(12):E690-7 (2012).

Zhao et al., "Organizing DNA origami tiles into larger structure suing pre-formed scaffold frames", Nano Lett. vol. 11(7):2997-3002 (2011).

Zhao et al., "Temperature-, light-, and host-molecule-responsive polymers with UCST behavior for aqueous sensing applications", ACS Appl. Polym. Mater, vol. 2:256-262 (2020).

International Search Report and Written Opinion in application No. PCT/US2023/032184, dated Dec. 7, 2023, in 15 pages.

International Preliminary Report on Patentability and Written Opinion in application No. PCT/US2023/032184, dated Mar. 1, 2025, in 8 pages.

* cited by examiner

POLYPEPTIDE CAPTURE, IN SITU FRAGMENTATION AND IDENTIFICATION

CROSS-REFERENCE TO RELATED APPLICATIONS

This application is a continuation application of U.S. application Ser. No. 18/463,063, filed Sep. 7, 2023, which claims priority to U.S. Provisional Application No. 63/377,249, filed on Sep. 27, 2022, each of which is incorporated herein by reference in their entirety.

BACKGROUND

Tools for characterizing and quantifying proteome dynamics with single-molecule resolution stand to overcome myriad challenges in biomedicine, including the measurement of low abundance polypeptides in therapeutic development, discovery of biomarkers for clinically actionable maladies, and diagnosing patients in clinical settings. Additionally, such tools could provide insights into the molecular heterogeneity of populations of proteoforms, which is currently masked by bulk measurements employed in research and clinical settings. Proteomes are large and diverse, having hundreds of thousands of different polypeptides and a wide dynamic range in the level of each type of polypeptide. The number and diversity of polypeptides in the proteome of any biological system changes rapidly and extensively in response to the state of the system. Building tools to measure proteome dynamics with single-molecule resolution is challenging because both single-molecule sensitivity and a high dynamic range are desired to comprehensively analyze the complex mixtures of polypeptides in a proteome. Moreover, single molecule measurements are prone to stochastic effects that are not apparent when measuring ensembles of molecules. Polypeptides being relatively large molecules display highly variable structural dynamics, the result of which can manifest as high stochasticity in detection of these molecules individually. This in turn can impact the quality of assay results.

Proteome research is in need of an assay platform that is capable of measuring tens-of-billions of individual molecules in parallel with single-molecule sensitivity, as well as the accurate capture of both low-abundance and high-abundance polypeptides. The present disclosure addresses this need and provides other advantages as well.

SUMMARY

The present disclosure provides a method of identifying a polypeptide. The method can include steps of (a) attaching a polypeptide to a particle or solid support, thereby producing an immobilized polypeptide having a plurality of amino acids linked to the particle or solid support; (b) fragmenting the immobilized polypeptide, whereby the particle or solid support is attached to a set of fragments of the polypeptide; (c) performing a binding assay including contacting the set of fragments with a plurality of affinity reagents and detecting binding of affinity reagents of the plurality of affinity reagents to the set of fragments; and (d) identifying the polypeptide from results of the binding assay.

Optionally, a method of identifying polypeptides can include steps of (a) attaching a polypeptide to a particle or solid support, thereby producing an immobilized polypeptide having a plurality of amino acids linked to the particle or solid support; (b) performing a binding assay including contacting the immobilized polypeptide with a plurality of affinity reagents and detecting binding of affinity reagents of the plurality of affinity reagents to the polypeptide; (c) fragmenting the immobilized polypeptide, whereby the particle or solid support is attached to a set of fragments of the polypeptide; (d) performing a second binding assay including contacting the set of fragments with a plurality of affinity reagents and detecting binding of affinity reagents of the plurality of affinity reagents to the set of fragments; and (e) identifying the polypeptide from results of the binding assay and second binding assay.

Further optionally, a method of identifying a polypeptide can include steps of (a) attaching a polypeptide to a particle or solid support, wherein the polypeptide is from a biological sample, thereby producing an immobilized polypeptide having a plurality of amino acids linked to the particle or solid support; (b) fragmenting the immobilized polypeptide, whereby the particle or solid support is attached to a set of fragments of the polypeptide; (c) performing a binding assay including contacting the set of fragments with a plurality of affinity reagents and detecting binding of affinity reagents of the plurality of affinity reagents to the set of fragments; (d) identifying the polypeptide from results of the binding assay; (e) attaching a second polypeptide to a second particle or second solid support, wherein the second polypeptide is from the biological sample, thereby producing a second immobilized polypeptide comprising a plurality of amino acids linked to the second particle or second solid support; (f) fragmenting the second immobilized polypeptide, whereby the second particle is attached to a second set of fragments of the second polypeptide; and (g) performing a binding assay including contacting the second set of fragments with the plurality of affinity reagents and detecting binding of the affinity reagents of the plurality of affinity reagents to fragments of the second set of fragments.

The present disclosure further provides a method of identifying polypeptides, including steps of (a) attaching a plurality of polypeptides to a plurality of particles or to addresses on a solid support, thereby producing a plurality of immobilized polypeptides, each of the immobilized polypeptides having a plurality of amino acids linked to a particle of the plurality of particles or to an address on the solid support; (b) fragmenting the plurality of immobilized polypeptides, thereby producing a plurality of immobilized fragment sets, wherein the immobilized fragment sets remain attached to the particles or addresses via the linked amino acids; (c) performing a binding assay including contacting the plurality of immobilized fragment sets with a plurality of affinity reagents and detecting binding of the plurality of affinity reagents to the plurality of immobilized fragment sets; and (d) identifying polypeptides of the plurality of polypeptides from results of the binding assay.

INCORPORATION BY REFERENCE

All publications, patents, and patent applications cited in this specification are herein incorporated by reference to the same extent as if each individual publication, patent, or patent application was specifically and individually indicated to be incorporated by reference. To the extent any publications, patents, and patent applications incorporated by reference include material that contradicts the disclosure contained in the specification, the specification is intended to supersede and/or take precedence over any such contradictory material.

DETAILED DESCRIPTION

The present disclosure provides methods and compositions for detecting polymeric macromolecules. Macromolecules can be identified, characterized or quantified based on the detection results. For example, a macromolecule can be detected based on binding of affinity reagents to one or more portions of the macromolecule, wherein the affinity reagents have known affinity for structural motifs in the macromolecule. The methods and compositions of the present disclosure can be applied to a variety of polymeric macromolecules such as polypeptides, nucleic acids or polysaccharides. Configurations of the methods and compositions will be exemplified in the context of polypeptides for ease of demonstration. However, it will be understood that other polymeric macromolecules can be used instead of polypeptides.

Affinity reagents can be generated to bind a wide variety of amino acid motifs found in polypeptides. Moreover, target amino acid motifs can be readily identified for many polypeptides since their amino acid sequences are known or readily obtainable. Indeed, the availability of low-cost, high-throughput methods for sequencing the genes that encode polypeptides has provided amino acid sequences for the full complement of polypeptides in the proteomes of many biological systems of interest. However, a major ambiguity that can complicate the design and use of affinity reagents relates to knowing the overall structure of a polypeptide and which amino acid motifs are on a surface of the molecule that is accessible to binding affinity reagents versus motifs that are buried within the folds of the polypeptide structure. Polypeptides are relatively large polymeric molecules that fold into complex structures. The folds and overall structures for the vast majority of polypeptides found in biological systems are not yet known. Many polypeptides have resisted attempts at empirical structural determination, and reliable methods are not yet available for a priori prediction of fold or overall shape for most polypeptides even when the amino acid sequences for those polypeptides are known. In some cases, the accessibility of target motifs of a polypeptide can be increased by denaturing the polypeptide. However, target motifs can often remain inaccessible to affinity reagents even when the polypeptide is denatured, since denatured polypeptides tend to form molten globules in which particular motifs may have a tendency to remain within the globule and therefore inaccessible to affinity reagents.

Figure 1:
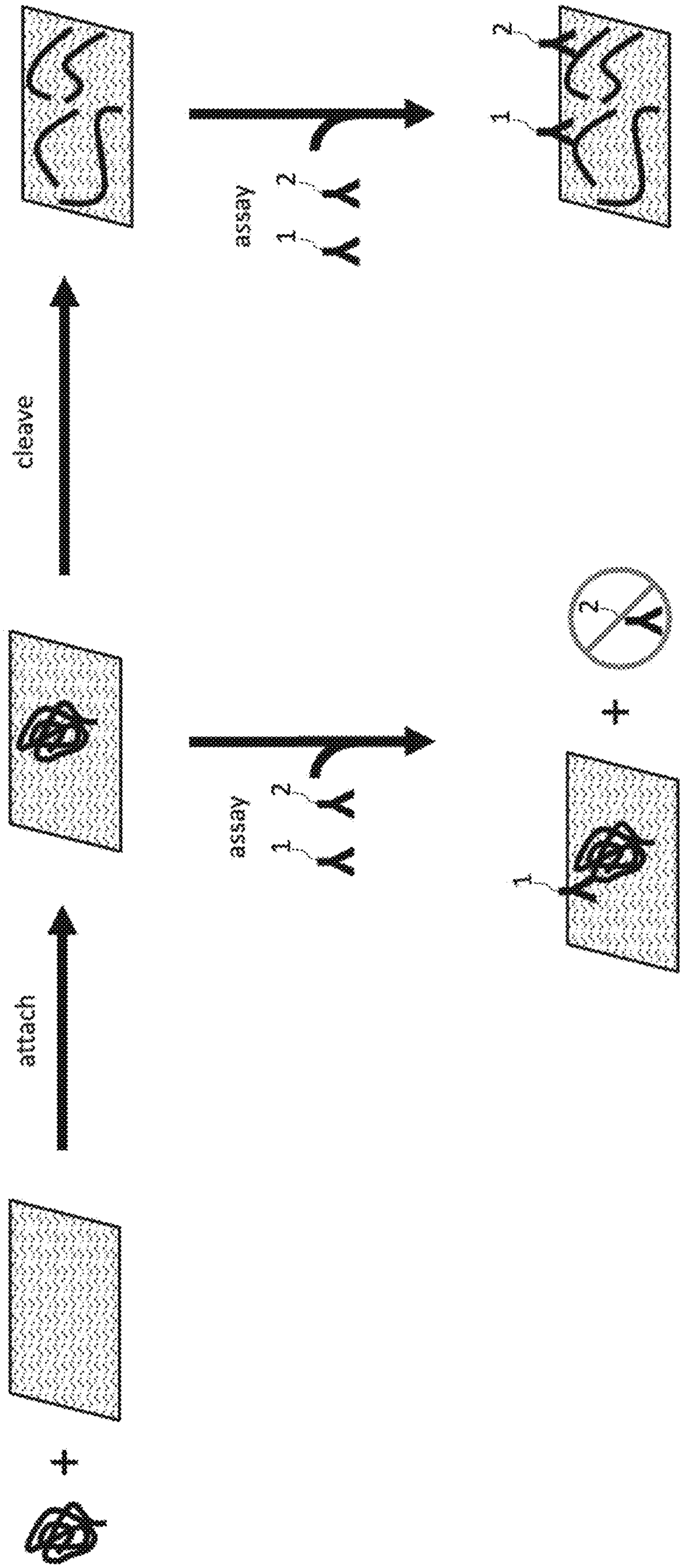
FIG. 1 shows a diagram of a process for cleaving an immobilized polypeptide, which is produced by attaching the polypeptide on the particle, to produce an immobilized set of polypeptide fragments and binding assays carried out on the immobilized polypeptide and immobilized set of polypeptide fragments.

The present disclosure provides compositions and methods that facilitate detection of macromolecules, such as polypeptides, by capturing individual macromolecules and cleaving each of the captured macromolecules to form a co-localized set of macromolecule fragments that can be bound to one or more affinity reagents. Returning to the example of a polypeptide, the overall structure of the polypeptide can be disrupted by cleaving it into fragments even though the fragments remain co-localized. As such, amino acid motifs that were buried in the structure of the intact polypeptide can be more accessible to affinity reagents in the set of polypeptide fragments. FIG. 1 provides an exemplary demonstration in which a polypeptide (represented as a globular squiggle) is attached to a particle (represented as a rectangle) and the polypeptide is contacted with two affinity reagents (labeled 1 and 2). Affinity reagent 1 binds to a surface accessible epitope on the polypeptide, but affinity reagent 2 is inhibited from binding its epitope which is buried within the globule. The polypeptide can be cleaved to form a set of polypeptide fragments that is attached to the particle. In the example of FIG. 1, both affinity reagents are able to bind the set of fragments since the epitopes for both are accessible following fragmentation.

The approach is particularly useful for multiplex assays wherein a large number and variety of polypeptides are detected in parallel. For example, a method of the present disclosure can be configured to individually capture polypeptides on respective particles to produce immobilized polypeptides, cleave each immobilized polypeptide to produce an immobilized set of polypeptide fragments on the respective particle, contact the set of polypeptide fragments with one or more affinity reagents, and detect binding between the affinity reagent(s) and the sets of polypeptide fragments. The polypeptides are distinguishable from each other due to their attachment to different particles. The accessibility of structural motifs within each polypeptide is increased by fragmenting the polypeptides on the particles. Because the set of fragments from a given polypeptide remain attached to their respective particles, characteristics detected for the set of fragments can be attributed to the given polypeptide.

The use of particles in methods and compositions of the present disclosure is exemplary. It will be understood that a particle can be replaced by a solid support. Moreover, a plurality of particles can be replaced by an array of addresses that separate polypeptides, and sets of fragments derived therefrom, on a solid support. In other configurations, the particles can be replaced by vessels, such as fluid droplets, that separate polypeptides from each other, and also separate sets of fragments derived therefrom, from each other. As such an individual address on a solid support or vessel can be configured to include structures or functions exemplified herein for particles.

Terms used herein will be understood to take on their ordinary meaning in the relevant art unless specified otherwise. Several terms used herein and their meanings are set forth below.

As used herein, the term "address" means a location in an array where a particular analyte (e.g. polypeptide or fragment thereof) is present. An address can contain a single analyte, or it can contain a population of several analytes of the same species (i.e. an ensemble of the analytes). Alternatively, an address can include a population of different analytes (e.g. a set of polypeptide fragments). Addresses are typically discrete. The discrete addresses can be contiguous, or they can be separated by interstitial spaces. An array useful herein can have, for example, addresses that are separated by less than 100 microns, 10 microns, 1 micron, 100 nm, 10 nm or less. Alternatively or additionally, an array can have addresses that are separated by at least 10 nm, 100 nm, 1 micron, 10 microns, or 100 microns. The addresses can each have an area of less than 1 square millimeter, 500 square microns, 100 square microns, 10 square microns, 1 square micron, 100 square nm or less. An array can include at least about $1\times10^4$, $1\times10^5$, $1\times10^6$, $1\times10^7$, $1\times10^8$, $1\times10^9$, $1\times10^{10}$, $1\times10^{11}$, $1\times10^{12}$, or more addresses. An address can be referred to as "unique" in reference to the association of the address with a particular analyte. The association may be permanent or transient. For example, an address may be unique to a polypeptide of interest during some or all steps of a method set forth herein.

As used herein, the term "affinity reagent" or "affinity agent" refers to a molecule or other substance that is capable of specifically or reproducibly binding to an analyte (e.g. polypeptide or fragment thereof) or moiety (e.g. post-translational modification of a polypeptide). An affinity agent can be larger than, smaller than or the same size as the analyte. An affinity agent may form a reversible or irreversible bond with an analyte. An affinity agent may bind with an analyte in a covalent or non-covalent manner. Affinity agents may include reactive affinity agents, catalytic affinity agents (e.g., kinases, proteases, etc.) or non-reactive affinity agents (e.g., antibodies or fragments thereof). An affinity agent can be non-reactive and non-catalytic, thereby not permanently altering the chemical structure of an analyte to which it binds. Affinity agents that can be particularly useful for binding to polypeptides include, but are not limited to, antibodies or functional fragments thereof (e.g., Fab' fragments, $F(ab')_2$ fragments, single-chain variable fragments (scFv), di-scFv, tri-scFv, or microantibodies), aptamers, affibodies, affilins, affimers, affitins, alphabodies, anticalins, avimers, miniproteins, DARPins, monobodies, nanoCLAMPs, lectins, or functional fragments thereof.

As used herein, the term "array" refers to a population of analytes (e.g. polypeptides) that are associated with unique identifiers such that the analytes can be distinguished from each other. A unique identifier can be a solid support, particle or bead, spatial address on a solid support, tag, label (e.g. luminophore), or barcode (e.g. nucleic acid barcode) that is associated with an analyte and that is distinct from other identifiers in the array. Analytes can be associated with unique identifiers by attachment, for example, via covalent or non-covalent bonds. An array can include different analytes that are each attached to different unique identifiers. An array can include different unique identifiers that are attached to the same or similar analytes. An array can include separate solid supports or separate addresses that each bear a different analyte, wherein the different analytes can be identified according to the locations of the solid supports or addresses.

As used herein, the term "attached" refers to the state of two things being joined, fastened, adhered, connected or bound to each other. For example, an analyte, such as a polypeptide, can be attached to a solid support or particle by a covalent or non-covalent bond. A covalent bond is characterized by the sharing of pairs of electrons between atoms. A non-covalent bond is a chemical bond that does not involve the sharing of pairs of electrons and can include, for example, hydrogen bonds, ionic bonds, van der Waals forces, hydrophilic interactions and hydrophobic interactions.

As used herein, the term "binding profile" refers to a plurality of binding outcomes for a polypeptide or other analyte. The binding outcomes can be obtained from independent binding observations, for example, independent binding outcomes can be acquired using different affinity agents, respectively. A binding profile can include empirical measurement outcomes, putative measurement outcomes or both. A binding profile can exclude empirical measurement outcomes or putative measurement outcomes.

The term "comprising" is intended herein to be open-ended, including not only the recited elements, but further encompassing any additional elements.

As used herein, the term "conformation," when used in reference to a molecule or particle, refers to the shape or proportionate dimensions of the molecule or particle. At the molecular level conformation can be characterized by the spatial arrangement of a molecule that results from the rotation of its atoms about their bonds. The conformation of a polypeptide can be characterized in terms of secondary structure, tertiary structure, or quaternary structure. Secondary structure of a polypeptide is the three-dimensional form of local segments of the polypeptide which can be defined, for example, by the pattern of hydrogen bonds between the amino hydrogen and carboxyl oxygen atoms in the peptide backbone or by the regular pattern of backbone dihedral angles in a particular region of the Ramachandran plot for the polypeptide. Tertiary structure of a polypeptide is the three-dimensional shape of a single polypeptide chain backbone including, for example, interactions and bonds of side chains that form domains. Quaternary structure of a polypeptide is the three-dimensional shape and interaction between the amino acids of multiple polypeptide chain backbones. A polypeptide having a given primary structure can have a native conformation in vitro, whereby the secondary and tertiary structures are the same as or substantially similar to the structures for a polypeptide having the same primary structure in vivo. Optionally the polypeptide can have the same quaternary structure in vivo and in vitro. Alternatively, a polypeptide having a given primary structure can have a denatured conformation in vitro, whereby the secondary, tertiary or quaternary structures are the same as or substantially similar to the structures for a polypeptide having the same primary structure in vivo. Moreover, a polypeptide having a given primary structure can have a denatured conformation in vitro, whereby the polypeptide lacks sufficient stability of secondary, tertiary or quaternary structure to perform biological function observed for a polypeptide having the same primary structure in vivo.

As used herein, the term “each,” when used in reference to a collection of items, is intended to identify an individual item in the collection but does not necessarily refer to every item in the collection. Exceptions can occur if explicit disclosure or context clearly dictates otherwise.

As used herein, the term “epitope” refers to an affinity target within a polypeptide, polypeptide fragment or other analyte. Epitopes may comprise amino acid sequences that are sequentially adjacent in the primary structure of a polypeptide or amino acids that are structurally adjacent in the secondary, tertiary or quaternary structure of a polypeptide. An epitope can optionally be recognized by or bound to an antibody. However, an epitope need not necessarily be recognized by any antibody, for example, instead being recognized by an aptamer, miniprotein or other affinity agent. An epitope can optionally bind an antibody to elicit an immune response. However, an epitope need not necessarily participate in, nor be capable of, eliciting an immune response.

As used herein, the term “exogenous,” when used in reference to a moiety of a molecule, means a moiety that is not present in a natural analog of the molecule. For example, an exogenous label of a polypeptide is a label that is not present on a naturally occurring polypeptide. Similarly, an exogenous reactive moiety that is present on a polypeptide is not found on the polypeptide in its native milieu.

As used herein, the term “immobilized,” when used in reference to a molecule that is in contact with a fluid phase, refers to the molecule being prevented from diffusing in the fluid phase. For example, immobilization can occur due to the molecule being confined at, or attached to, a solid phase. Immobilization can be temporary (e.g. for the duration of one or more steps of a method set forth herein) or permanent. Immobilization can be reversible or irreversible under conditions utilized for a method, system or composition set forth herein.

As used herein, the term “label” refers to a molecule or moiety thereof that provides a detectable characteristic. The detectable characteristic can be, for example, an optical signal such as absorbance of radiation, luminescence (e.g. fluorescence) emission, luminescence lifetime or luminescence polarization; Rayleigh and/or Mie scattering; binding affinity for a ligand or receptor; magnetic properties; electrical properties; charge; mass; radioactivity or the like. Exemplary labels include, without limitation, a fluorophore, luminophore, chromophore, nanoparticle (e.g., gold, silver, carbon nanotubes), heavy atom, radioactive isotope, mass label, charge label, spin label, receptor, ligand, or the like. Nucleic acids can be used as labels and distinguished from each other based on unique nucleotide sequences. The unique nucleotide sequences can function as tags for identifying the molecule or moiety to which the nucleic acid is attached or otherwise associated.

As used herein, the term “linked,” when used in reference to two objects or moieties, means the two objects or moieties are attached to each other via a linker. The linker can be directly attached to an object or moiety, for example, via a covalent or non-covalent bond.

As used herein, the term “linker” refers to a moiety that connects two objects to each other. One or both objects can be a molecule, solid support, address, particle or bead. Both objects can be moieties of a molecule, solid support, address, particle or bead. The term can also refer to an atom, moiety or molecule that is configured to react with two objects to form a moiety that connects the two objects. The connection of a linker to one or both objects can be a covalent bond or non-covalent bond. A linker may be configured to provide a chemical or mechanical property to the moiety connecting two objects, such as hydrophobicity, hydrophilicity, electrical charge, polarity, rigidity, or flexibility. A linker may comprise two or more functional groups that facilitate coupling of the linker to the first and second objects. A linker may include a polyfunctional linker such as a homobifunctional linker, heterobifunctional linker, homopolyfunctional linker, or heteropolyfunctional linker. Exemplary compositions for linkers can include, but are not limited to, a polyethylene glycol (PEG), polyethylene oxide (PEO), amino acid, polypeptide, nucleotide, nucleic acid, nucleic acid origami, dendrimer, protein nucleic acid (PNA), polysaccharide, carbon, nitrogen, oxygen, ether, sulfur, or disulfide. A linker can be a bead or particle such as a structured nucleic acid particle.

As used herein, the term “measurement outcome” refers to information resulting from observation or examination of a process. For example, the measurement outcome for contacting an affinity agent with an analyte, such as a polypeptide or fragment thereof, can be referred to as a “binding outcome.” A measurement outcome can be positive or negative. For example, observation of binding is a positive binding outcome and observation (or perception) of non-binding is a negative binding outcome. A measurement outcome can be a null outcome in the event a positive or negative outcome does not result from a given measurement.

As used herein, the term “moiety” refers to a component or part of a molecule. The term do not necessarily denote the relative size of the component or part compared to the rest of the molecule, unless indicated otherwise. A moiety can contain one or more atom. As used herein, the term “attachment moiety” refers to a component or part of a molecule that is configured to attach the molecule to another object or substance. The other object or substance can be, for example, a solid support, particle or second molecule. An attachment moiety can participate in a covalent or non-covalent bond.

As used herein, the term “nucleic acid nanoball” refers to a globular or spherical nucleic acid structure. A nucleic acid nanoball may comprise a concatemer of sequence regions that arranges in a globular structure. A nucleic acid nanoball may include DNA, RNA, PNA, modified or non-natural nucleic acids, or combinations thereof. A nucleic acid nanoball can have a compact structure, thereby forming a structured nucleic acid particle (SNAP) or portion thereof.

As used herein, the term “nucleic acid origami” refers to a nucleic acid construct comprising engineered tertiary or quaternary structure(s), optionally, in addition to any double stranded helical structure occurring in complementary strands of the nucleic acid construct. A nucleic acid origami may include DNA, RNA, PNA, modified or non-natural nucleic acids, or combinations thereof. A nucleic acid origami may include a plurality of oligonucleotides that hybridize via sequence complementarity to produce the engineered structure of the origami particle. A nucleic acid origami may include sections of single-stranded or double-stranded nucleic acid, or combinations thereof. Exemplary nucleic acid origami structures may include nanotubes, nanowires, cages, tiles, nanospheres, blocks, and combinations thereof. A nucleic acid origami can optionally include a relatively long scaffold nucleic acid to which multiple smaller nucleic acids hybridize, thereby creating folds and bends in the scaffold that produce an engineered structure. The scaffold nucleic acid can be circular or linear. The scaffold nucleic acid can be single stranded but for hybridization to the smaller nucleic acids. A smaller nucleic acid (sometimes referred to as a "staple") can hybridize to two regions of the scaffold, wherein the two regions of the scaffold are separated by an intervening region that does not hybridize to the smaller nucleic acid.

As used herein, the term "orthogonal," when used in reference to a first reagent in view of a second reagent, refers to modification of the first reagent in reaction conditions that do not substantially modify the second reagent. For example, a first reagent or moiety can be considered orthogonal to a second reagent or moiety if the first reagent or moiety can be chemically modified in the presence of the second reagent or moiety without modifying the second reagent or moiety. A first reagent or moiety can be considered orthogonal to a second reagent or moiety if the second reagent or moiety is inert to reaction conditions used to chemically modify the first reagent or moiety. A first reaction can be considered orthogonal to a given molecule or moiety when the given molecule or moiety is reactive in a second reaction after having been subjected to the conditions of the first reaction.

As used herein, the term "particle" means an object having a largest dimension between 50 nm and 1 mm. The object can be composed of a rigid or semi-rigid material. The particle can be insoluble in a fluid such as aqueous liquid. A particle can have a shape characterized, for example, as a sphere, ovoid, polyhedron, or other recognized shape whether having regular or irregular dimensions. Exemplary particles include, but are not limited to, structured nucleic acid particles (SNAPs) such as nucleic acid origami particles; optically detectable particles such as fluorescent nanoparticles, FluoSpheres™, and quantum dots; organic particles; inorganic particles; gel particles; or particles made from solid support materials set forth herein or known in the art.

As used herein, the term "polypeptide" refers to a molecule comprising two or more amino acids joined by a peptide bond. A polypeptide may also be referred to as a protein, oligopeptide or peptide. Although the terms "protein," "polypeptide," "oligopeptide" and "peptide" may optionally be used to refer to molecules having different characteristics, such as amino acid sequence composition or length, molecular weight, origin of the molecule or the like, the terms are not intended to inherently include such distinctions in all contexts. A polypeptide can be a naturally occurring molecule, or synthetic molecule. A polypeptide may include one or more non-natural amino acids, modified amino acids, or non-amino acid linkers. A polypeptide may contain D-amino acid enantiomers, L-amino acid enantiomers or both. Amino acids of a polypeptide may be modified naturally (e.g. by a post-translational modification) or synthetically (e.g. by a functional moiety).

As used herein, the term "pool," when used in reference to a plurality of objects or molecules, refers to the objects or molecules being in fluidic communication with each other. A pool can include a fluid phase and optionally the fluid phase can be in contact with a solid phase. For example, the solid phase can include immobilized objects or substances that are in communication with fluid-phase objects or substances. Objects in a substance or pool can be, but need not be, spatially distinguishable from each, for example, when detected in a method set forth herein. As such, the objects or substances can be detected as an ensemble in a method set forth herein.

As used herein, the term "random," when used in reference to an array, means the identities of analytes at particular addresses are not known. In some cases, an array can be referred to as random to indicate a mode of manufacture in which the identities of analytes at the addresses were not known from the manufacturing process. Optionally, the identity of the analyte can be unknown for at least 55%, 75%, 90%, 95% or 99% of the addresses in a random array. The addresses in a random array can be arranged in a repeating pattern such as a hexagonal grid or rectilinear grid. Alternatively or additionally, the addresses in a random array can be arranged in a non-repeating pattern or irregular pattern.

As used herein the term "set of polypeptide fragments" or "set of fragments" refers to a plurality of polypeptide fragments derived from cleaving a single polypeptide. The plurality of polypeptide fragments can be immobilized, for example, being attached to a particle or to an address in an array. The plurality of polypeptide fragments can include substantially all of the amino acid sequence content of the polypeptide from which it is derived. Optionally, the plurality of polypeptide fragments can include a fraction of the amino acid sequence content of the polypeptide from which it is derived. The fraction can include, for example, at least 50%, 60%, 70%, 80%, 90%, 95% or more of the amino acid sequence content of the polypeptide from which the plurality of fragments is derived.

As used herein, the term "single," when used in reference to an analyte, refers to the analyte (e.g. polypeptide, nucleic acid, or affinity agent) being individually manipulated or distinguished from other analytes. A single analyte can be a single molecule (e.g. single polypeptide), a single complex of two or more molecules (e.g. a single polypeptide attached to a structured nucleic acid particle, or a single polypeptide bound to an affinity agent), a single particle, or the like. A single analyte may be resolved from other analytes based on, for example, spatial or temporal separation from the other analytes. Accordingly, an analyte can be detected at "single-analyte resolution" which is the detection of, or ability to detect, the analyte on an individual basis, for example, as distinguished from its nearest neighbor in an array. Reference herein to a 'single analyte' in the context of a composition, apparatus or method does not necessarily exclude application of the composition, apparatus or method to multiple single analytes that are manipulated or distinguished individually, unless indicated contextually or explicitly to the contrary.

As used herein, the term "solid support" refers to a substrate that is insoluble in aqueous liquid. Optionally, the substrate can be rigid. The substrate can be non-porous or porous. The substrate can optionally be capable of taking up a liquid (e.g. due to porosity) but will typically, but not necessarily, be sufficiently rigid that the substrate does not swell substantially when taking up the liquid and does not contract substantially when the liquid is removed. A non-porous solid support is generally impermeable to liquids or gases. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides etc.), nylon, ceramics, resins, Zeonor™, silica or silica-based materials including silicon and modified silicon, carbon, metals, inorganic glasses, optical fiber bundles, gels, and polymers. In particular configurations, a flow cell contains the solid support such that fluids introduced to the flow cell can interact with a surface of the solid support to which one or more components of a binding event (or other reaction) is attached.

As used herein, the term "structured nucleic acid particle" (or "SNAP") refers to a single- or multi-chain polynucleotide molecule having a compacted three-dimensional structure. The compacted three-dimensional structure can optionally be characterized in terms of hydrodynamic radius or Stoke's radius of the SNAP relative to a random coil or other non-structured state for a nucleic acid having the same sequence length as the SNAP. The compacted three-dimensional structure can optionally be characterized with regard to tertiary structure. For example, a SNAP can be configured to have an increased number of internal binding interactions between regions of a polynucleotide strand, less distance between the regions, increased number of bends in the strand, and/or more acute bends in the strand, as compared to the same nucleic acid molecule in a random coil or other non-structured state. Alternatively or additionally, the compacted three-dimensional structure can optionally be characterized with regard to quaternary structure. For example, a SNAP can be configured to have an increased number of interactions between polynucleotide strands or less distance between the strands, as compared to the same nucleic acid molecule in a random coil or other non-structured state. In some configurations, the secondary structure (i.e. the helical twist or direction of the polynucleotide strand) of a SNAP can be configured to be more dense than the same nucleic acid molecule in a random coil or other non-structured state. A SNAP can optionally be modified to permit attachment of additional molecules to the SNAP. A SNAP may contain DNA, RNA, PNA, modified or non-natural nucleic acids, or combinations thereof. A SNAP may include a plurality of oligonucleotides that hybridize to form the SNAP structure. The plurality of oligonucleotides in a SNAP may include oligonucleotides that are conjugated to other molecules (e.g., affinity reagents, detectable labels) or are configured to be conjugated to other molecules (e.g., by reactive handles). A SNAP may include engineered or rationally-designed structures, such as nucleic acid origami.

As used herein, the term "unique identifier" refers to a moiety, object or substance that is associated with an analyte and that is distinct from other identifiers, throughout one or more steps of a process. The moiety, object or substance can be, for example, a solid support such as a particle or bead; a location on a solid support; a spatial address in an array; a tag; a label such as a luminophore; a molecular barcode such as a nucleic acid having a unique nucleotide sequence or a protein having a unique amino acid sequence; or an encoded device such as a radiofrequency identification (RFID) chip, electronically encoded device, magnetically encoded device or optically encoded device. The process in which a unique identifier is used can be an analytical process, such as a method for detecting, identifying, characterizing or quantifying an analyte; a separation process in which at least on analyte is separated from other analytes; or a synthetic process in which an analyte is modified or produced. The unique identifier can be associated with an analyte via immobilization. For example, a unique identifier can be covalently or non-covalently attached to an analyte. A unique identifier can be exogenous to an associated analyte, for example, being synthetically attached to the associated analyte. Alternatively, a unique identifier can be endogenous to the analyte, for example, being attached or associated with the analyte in the native milieu of the analyte.

As used herein, the term "vessel" refers to an enclosure that contains a substance. The enclosure can be permanent or temporary with respect to the timeframe of a method set forth herein or with respect to one or more steps of a method set forth herein. Exemplary vessels include, but are not limited to, a well (e.g. in a multiwell plate or array of wells), test tube, channel, tubing, pipe, flow cell, bottle, vesicle, droplet that is immiscible in a surrounding fluid, or the like. A vessel can be entirely sealed to prevent fluid communication from inside to outside, and vice versa. Alternatively, a vessel can include one or more ingress or egress to allow fluid communication between the inside and outside of the vessel. For example, a vessel can be porous, wherein the pores allow passage of some substances without allowing passage of a substance of interest such as an analyte of interest. A vessel can be made from multiple materials, for example, including a well in a solid support that is covered by a seal such as a wax or fluid that is immiscible with fluid in the well.

The embodiments set forth below and recited in the claims can be understood in view of the above definitions.

The present disclosure provides a method of identifying a polypeptide. The method can include steps of (a) attaching a polypeptide to a particle, thereby producing an immobilized polypeptide having a plurality of amino acids linked to the particle; (b) fragmenting the immobilized polypeptide, whereby the particle is attached to a set of fragments of the polypeptide; (c) performing a binding assay including contacting the set of fragments with a plurality of affinity reagents and detecting binding of affinity reagents of the plurality of affinity reagents to the set of fragments; and (d) identifying the polypeptide from results of the binding assay.

A polypeptide can be derived from a natural or synthetic source. Exemplary sources include, but are not limited to a biological tissue, fluid, cell or subcellular compartment (e.g. organelle). For example, a sample can be derived from a tissue biopsy, biological fluid (e.g. blood, plasma, extracellular fluid, urine, mucus, saliva, semen, vaginal fluid, sweat, synovial fluid, lymph, cerebrospinal fluid, peritoneal fluid, pleural fluid, amniotic fluid, intracellular fluid, extracellular fluid, etc.), fecal sample, hair sample, cultured cell, culture media, fixed tissue sample (e.g. fresh frozen or formalin-fixed paraffin-embedded) or polypeptide synthesis reaction. Any sample where a polypeptide is a native or expected constituent can be used. For example, sources for gastric enzymes may include cells from digestive organs, a sample from a gastric duct, or a fluid sample from a digestive organ (e.g., bile). In a second example, a primary source for a cancer biomarker polypeptide may be a tumor biopsy sample. Other sources include environmental samples or forensic samples.

Exemplary organisms from which a polypeptide can be derived include, for example, a mammal such as a rodent, mouse, rat, rabbit, guinea pig, ungulate, horse, sheep, pig, goat, cow, cat, dog, primate, non-human primate or human; a plant such as *Arabidopsis thaliana*, tobacco, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a *Dictyostelium discoideum*; a fungi such as *Pneumocystis carinii, Takifugu rubripes*, yeast, *Saccharamoyces cerevisiae* or *Schizosaccharomyces pombe*; or a

*Plasmodium falciparum*. A polypeptide can also be derived from a prokaryote such as a bacterium, *Escherichia coli*, staphylococci or *Mycoplasma pneumoniae*; an archae; a virus such as Hepatitis C virus, influenza virus, coronavirus, or human immunodeficiency virus; or a viroid. A polypeptide can be derived from a homogeneous culture or population of the above organisms or alternatively from a collection of several different organisms, for example, in a community or ecosystem.

In some cases, a polypeptide can be derived from an organism that is collected from a host organism. A polypeptide may be derived from a parasitic, pathogenic, symbiotic, or latent organism collected from a host organism. A polypeptide can be derived from an organism, tissue, cell or biological fluid that is known or suspected of being associated with a disease state or disorder (e.g., an oncogenic virus). Alternatively, a polypeptide can be derived from an organism, tissue, cell or biological fluid that is known or suspected of not being associated with a particular disease state or disorder. For example, one or more polypeptides isolated from such a source can be used as a control for comparison to results acquired from a source that is known or suspected of being associated with the particular disease state or disorder. A sample may include a microbiome. A sample may include a plurality of polypeptides contributed by microbiome constituents. In some cases, one or more polypeptides used in a method, composition or apparatus set forth herein may be obtained from a single organism (e.g. an individual human), single cell, single organelle, or single polypeptide-containing particle (e.g., a viral particle).

In some cases, one or more polypeptides can be obtained from a single cell, polypeptide-containing particle (e.g., a viral particle), or a fragment thereof. A single cell, polypeptide-containing particle, or fragment thereof may be collected by any known method in the art, such as fluorescence assisted cell sorting, magnetic-assisted cell sorting, and buoyancy-assisted cell sorting. In some cases, a single cell, polypeptide-containing particle, or fragment thereof may be collected by an emulsion technique such as liposome or micellar capture.

A polypeptides can optionally be separated or isolated from other components of the source for the polypeptide(s). For example, one or more polypeptides can be separated or isolated from lipids, nucleic acids, hormones, enzyme cofactors, vitamins, metabolites, microtubules, organelles (e.g. nucleus, mitochondria, chloroplast, endoplasmic reticulum, vesicle, cytoskeleton, vacuole, lysosome, cell membrane, cytosol or Golgi apparatus), other polypeptides or the like. Polypeptide separation can be carried out using methods known in the art such as centrifugation (e.g. to separate membrane fractions from soluble fractions), density gradient centrifugation (e.g. to separate different types of organelles), precipitation, affinity capture, adsorption, liquid-liquid extraction, solid-phase extraction, chromatography (e.g. affinity chromatography, ion exchange chromatography, reverse phase chromatography, size exclusion chromatography, electrophoresis (e.g. polyacrylamide gel electrophoresis) or the like. Particularly useful polypeptide separation methods are set forth in Scopes, *Polypeptide Purification Principles and Practice*, Springer; 3rd edition (1993).

A polypeptide can be in a native conformation or denatured conformation. For example, a polypeptide can be in a native conformation, whereby it is capable of performing native function(s) such as catalysis of its natural substrates or binding to its natural substrates. Alternatively, a polypeptides can be in a denatured conformation such that it is incapable of performing native function(s) such as catalysis of its natural substrates or binding to its natural substrates. A polypeptide can be in a native conformation for some manipulations set forth herein and in a denatured conformation for other manipulations set forth herein. A polypeptide may be denatured at any stage during manipulation, including for example, upon removal from a native milieu or at a later stage of processing such as a stage where the polypeptide is separated from other cellular components, fractionated from other polypeptides, functionalized to include a reactive moiety, attached to a particle or solid support, contacted with an affinity reagent, detected, digested to produce fragments, or other step set forth herein. A denatured polypeptide may be refolded, for example, reverting to a native state for one or more step of a process set forth herein.

A polypeptide can include two or more subunits that form a complex. For example, each of the subunits can have a primary structure that includes a polypeptide backbone connecting a single amino terminus to a single carboxy terminus. Two or more subunits that form a complex can interact with each other via non-covalent bonding. The two or more subunits that form a complex can be relatively stable such that the subunits are associated with each other more often than they are dissociated from each other in vivo and/or in vitro. For example, hemoglobin is known to typically exist as a complex of two pairs of different polypeptide strands. Specifically, each pair includes an alpha chain and a beta chain, such that the quaternary structure of the hemoglobin polypeptide includes two alpha chains and two beta chains Alternatively, two or more subunits can form a stable, yet transient, complex under some conditions. For example, a G protein-coupled receptor (GPCR) can associate with a G-protein, thereby forming a complex that transduces a signal in a cell, and the GPCR can dissociate from the G-protein to pause transduction of the signal.

In some cases, two or more subunits can be covalently attached to each other in a complex. For example, a disulfide bridge can form between cysteine residues on respective polypeptide subunits. Alternatively or additionally, two or more subunits can be synthetically crosslinked to each other in a complex. Accordingly, a method set forth herein can include a step of reacting a polypeptide complex with a crosslinking reagent to form one or more crosslinks between subunits of the complex. Any of a variety of crosslinking agents can be used including, for example, those that are available commercially (e.g. from ThermoFisher, Waltham MA or Sigma Aldrich, St. Louis, MO) or set forth herein. Cleavable crosslinkers can be useful, for example, to facilitate separation of crosslinked species for one or more steps of a method set forth herein.

Any of a variety of particles can be used in a method or composition set forth herein. Structured nucleic acid particles are particularly useful such as those that include nucleic acid origami. A nucleic acid origami can include one or more nucleic acids having a variety of overall shapes such as a disk, tile, sphere, cuboid, tubule, pyramid, polyhedron, or combination thereof. Examples of structures formed with DNA origami are set forth in Zhao et al. *Nano Lett.* 11, 2997-3002 (2011); Rothemund *Nature* 440:297-302 (2006); Sigle et al, *Nature Materials* 20:1281-1289 (2021); or U.S. Pat. No. 8,501,923 or 9,340,416, each of which is incorporated herein by reference. In some configurations, a nucleic acid origami may include a scaffold nucleic acid and a plurality of staple nucleic acids. The scaffold can be configured as a single, continuous strand of nucleic acid, and the staples can be formed by nucleic acids that hybridize, in whole or in part, with the scaffold nucleic acid. A particle including one or more nucleic acids (e.g. as found in origami or nanoball structures) may include regions of single-stranded nucleic acid, regions of double-stranded nucleic acid, or combinations thereof.

In some configurations, a nucleic acid origami includes a scaffold composed of a nucleic acid strand to which a plurality of oligonucleotides is hybridized. A nucleic acid origami may have a single scaffold molecule or multiple scaffold molecules. A scaffold nucleic acid can be linear (i.e. having a 3' end and 5' end) or circular (i.e. closed such that the scaffold lacks a 3' end and 5' end). A nucleic acid scaffold can be derived from a natural source, such as a viral genome or a bacterial plasmid. For example, a nucleic acid scaffold can include a single strand of an M13 viral genome. In other configurations, a nucleic acid scaffold may be synthetic, for example, having a non-naturally occurring sequence in full or in part. A scaffold nucleic acid can be single stranded but for a plurality of oligonucleotides hybridized thereto or short regions of internal complementarity. The size of a nucleic acid scaffold may vary to accommodate different uses. For example, a nucleic acid scaffold may include at least about 100, 500, 1000, 2500, 5000 or more nucleotides. Alternatively or additionally, a nucleic acid scaffold may include at most about 5000, 2500, 1000, 500, 100 or fewer nucleotides.

A nucleic acid origami can include a plurality of oligonucleotides that are hybridized to a scaffold nucleic acid. A first region of an oligonucleotide sequence can be hybridized to a scaffold nucleic acid while a second region is not hybridized to the scaffold. One or both of the regions can be located at or near the 5' end of the oligonucleotide, at or near the 3' end of the oligonucleotide, or in a region of the oligonucleotide that is between the end regions. The second region can be in a single stranded state or, alternatively, can participate in a hairpin or other self-annealed structure in the oligonucleotide. Optionally, the second region of the oligonucleotide can include an attachment moiety that is configured to form a covalent or non-covalent bond with a reactive moiety, such as an amino acid of a polypeptide. As set forth in further detail herein, an attachment moiety of a particle can bond with a reactive moiety of a polypeptide or fragment thereof. In some cases, the second region of the oligonucleotide can hybridize to a complementary oligonucleotide to form a double-stranded region. The first and second regions of the oligonucleotide can be adjacent to each other in the oligonucleotide sequence or separated by a spacer region. The spacer region can be single stranded, for example, to provide relative flexibility. Alternatively, the spacer region can be double stranded or at least partially double stranded, for example, to provide relative rigidity.

An oligonucleotide can include two sequence regions that are hybridized to a scaffold nucleic acid, for example, to function as a 'staple' that restrains the structure of the scaffold. For example, a single oligonucleotide can hybridize to two regions of a scaffold that are separated from each other in the primary sequence of the scaffold. As such, the oligonucleotide can function to retain those two regions of the scaffold in proximity to each other or to otherwise constrain the scaffold to a desired conformation. Two sequence regions of an oligonucleotide staple can be adjacent to each other in the oligonucleotide sequence or separated by a spacer region that does not hybridize to the scaffold. One or more regions of an oligonucleotide that hybridize to a scaffold nucleic acid can be located at or near the 5' end of the oligonucleotide, at or near the 3' end of the oligonucleotide, or in a region of the oligonucleotide that is between the end regions. Oligonucleotides can be configured to hybridize with a nucleic acid scaffold, another oligonucleotide, a staple oligonucleotide, or a combination thereof. The oligonucleotides can be linear (i.e. having a 3' end and a 5' end) or closed (i.e. circular, lacking both 3' and 5' ends).

An oligonucleotide that is included in a nucleic acid origami can have any of a variety of lengths. An oligonucleotide may have a length of at least about 10, 25, 50, 100, 250, 500, or more nucleotides. Alternatively or additionally, an oligonucleotide may have a length of no more than about 500, 250, 100, 50, 25, 10, or fewer nucleotides. An oligonucleotide in a nucleic acid origami may hybridize with another oligonucleotide or a scaffold strand forming a particular number of base pairs. An oligonucleotide may form a hybridization region of at least about 5, 6, 7, 8, 9, 10, 15, 20, 25, 50 or more consecutive or total base pairs. Alternatively or additionally, an oligonucleotide may form a hybridization region of no more than about 50, 25, 20, 15, 10, 9, 8, 7, 6, 5, or fewer consecutive or total base pairs.

A reactive moiety, attachment moiety, polypeptide, polypeptide fragment or other moiety can be attached to nucleic acid origami via a scaffold component or oligonucleotide component of the origami structure. For example, the scaffold or oligonucleotide can include one or more nucleotide analog(s) that attach(es) covalently or non-covalently to a reactive moiety, attachment moiety, polypeptide, polypeptide fragment or other moiety. A nucleic acid origami can include one or more oligonucleotides components each having a reactive moiety, attachment moiety, polypeptide, polypeptide fragment or other moiety. A nucleic acid origami, or other particle set forth herein, can include at least 1, 2, 5, 10, 20, 30, 40, 50, 75, 100 or more moieties of a type set forth herein (e.g. attachment moieties). Alternatively or additionally, a nucleic acid origami, or other particle set forth herein, can include at most 100, 75, 50, 40, 30, 20, 10, 5, 2, or 1 moieties of a type set forth herein (e.g. attachment moieties).

A structured nucleic acid particle (e.g., nucleic acid origami, or nucleic acid nanoball) may be formed by an appropriate technique including, for example, those known in the art. Nucleic acid origami can be designed, for example, as described in Rothemund, *Nature* 440:297-302 (2006), or U.S. Pat. No. 8,501,923 or 9,340,416, each of which is incorporated herein by reference. Nucleic acid origami may be designed using a software package, such as CADNANO (cadnano.org), ATHENA (github.com/lcbb/athena), or DAEDALUS (daedalus-dna-origami.org).

Another type of structured nucleic acid particle is a nucleic acid nanoball. Nucleic acid nanoballs may be fabricated by a method such as rolling circle amplification using a circular template to generate a nucleic acid amplicon consisting of a concatemer of template complements. The amplicon can be further modified to include crosslinks, for example, in the form of staples that hybridize to different regions of the amplicon. Exemplary methods for making nucleic acid nanoballs are described, for example, in U.S. Pat. No. 8,445,194, which is incorporated herein by reference.

Further examples of structured nucleic acid particles that include nucleic acid origami or nanoballs are set forth, for example, in U.S. Pat. No. 11,203,612; US Pat. App. Pub. No. 2022/0162684 A1 or U.S. Pat. No. 11,505,796 (U.S. patent application Ser. No. 17/692,035), each of which is incorporated herein by reference.

A particle need not be composed primarily of nucleic acid and, in some cases, may be devoid of nucleic acids. For example, a particle can be composed of a solid support material, such as a silicon or silica nanoparticle, a carbon nanoparticle, a cellulose nanobead, a PEG nanobead, a polymeric nanoparticle (e.g., polyethyleneimine, dendritic polymer, dendrimer, polyacrylate particle, polystyrene-based particle, FluoSphere™, etc.), upconversion nanocrystal, or a quantum dot. A particle may include solid materials and shell-like materials (e.g., carbon nanospheres, silicon oxide nanoshells, iron oxide nanospheres, polymethylmethacrylate nanospheres, etc.). A particle may include distinct surfaces, such as plates or shells. In some configurations, a particle may include a gel material.

A particle may have any of a variety of sizes and shapes to accommodate use in a desired application. For example, a particle can have a regular or symmetric shape or, alternatively, a particle can have an irregular or asymmetric shape. The shape can be rigid or pliable. The size or shape of a particle can be characterized with respect to length, area, or volume. The length, area or volume can be characterized in terms of a minimum, maximum, or average for a population. Optionally, a particle can have a minimum, maximum or average length of at least about 50 nm, 100 nm, 250 nm, 500 nm, 1 μm, 5 μm or more. Alternatively or additionally, a particle can have a minimum, maximum or average length of no more than about 5 μm, 1 μm, 500 nm, 250 nm, 100 nm, 51 nm, or less. Optionally, a particle can have a minimum, maximum or average volume of at least about 1 $\mu m^3$, 10 $\mu m^3$, 100 $\mu m^3$, 1 $mm^3$ or more. Alternatively or additionally, a particle can have a minimum, maximum or average volume of no more than about 1 $mm^3$, 100 $\mu m^3$, 10 $\mu m^3$, 1 $\mu m^3$ or less.

A particle can be characterized with respect to its footprint (e.g. occupied area on a surface). The footprint may have a regular shape or an approximately regular shape, such as triangular, square, rectangular, circular, ovoid, or polygon. Optionally, the minimum, maximum or average area for a particle footprint can be at least about 10 $nm^2$, 100 $nm^2$, 1 $\mu m^2$, 10 $\mu m^2$, 100 $\mu m^2$, 1 $mm^2$ or more. Alternatively or additionally, the minimum, maximum or average area for a particle footprint can be at most about 1 $mm^2$, 100 $\mu m^2$, 10 $\mu m^2$, 1 $\mu m^2$, 100 $nm^2$, 10 $nm^2$, or less.

A particle that is made or used in a method set forth herein can be suspended in a fluid, immobilized on a solid support, or immobilized in another material such as a gel or solid support material. For example, a population of particles can be colloidal for some, or all steps of a method set forth herein. Alternatively, a population of particles can be immobilized in, or on a solid support for some, or all steps of a method set forth herein.

The use of particles in methods and compositions of the present disclosure is exemplary. Particles can be advantageous for example to provide for three-dimensional diffusion in a fluid-phase. However, particles need not be used. It will be understood that a particle can be replaced with a solid support in a method or composition set forth herein. In some configurations, particles can be replaced by an array of addresses on a solid support. As such an individual address on a solid support can be configured to include a structure or function exemplified herein for particles. For example, one or more addresses in an array on a solid support can be configured to attach polypeptides and sets of polypeptide fragments, and affinity reagents can be bound to polypeptides or fragments thereof at the address(es).

A method of the present disclosure can include a step of attaching a polypeptide to a particle. A polypeptide that is to be attached to a particle can include at least one amino acid that is reactive with an attachment moiety on the particle. Optionally, attachment can exploit a reactive moiety that is present in a natural amino acid. For example, attachment can occur between an attachment moiety on a particle and (A) an amine that is present at the amino terminus of a polypeptide or in the side chain of a lysine, histidine or arginine side chain; (B) a sulfur that is present in the side chain of a cysteine or methionine; (C) a carboxylate that is present at the carboxy terminus of a polypeptide or in the side chain of an aspartic acid or glutamic acid; (D) an oxygen that is present in the side chain of a serine, threonine or tyrosine; or (E) an amide that is present in the side chain of a glutamine or asparagine. A polypeptide can include a plurality of amino acids of a given type, such as those identified above, that are reactive with an attachment moiety on a particle. In some cases, two or more types of amino acids on a polypeptide can participate in forming links to a particle. For example, the two or more types of amino acids can be reactive with one or more types of attachment moieties on the particle.

Optionally, a polypeptide can be modified to incorporate an exogenous moiety that is reactive with an attachment moiety on a particle. For example, one or more amino acids of a polypeptide can be modified to include an exogenous moiety that forms a covalent bond with a chemically reactive attachment moiety on a particle. Optionally, one or more amino acids of a polypeptide can be modified to include an exogenous moiety that participates in a binding reaction to form a non-covalent bond with an attachment moiety on a particle. An amino acid can be functionalized with an exogenous moiety by exploiting reactivities of amines, sulfurs, carboxylates, oxygens, amides or other reactive moieties found in native amino acids. Exemplary reactive moieties (e.g. native or exogenous to polypeptides) and attachment moieties with which they react are set forth below or in WO 2019/195633 A1; US Pat. App. Pub. No. 2021/0101930 A1; U.S. Pat. No. 11,203,612; US Pat. App. Pub. No. 2022/0162684 A1; or U.S. Pat. No. 11,505,796 (U.S. patent application Ser. No. 17/692,035), each of which is incorporated herein by reference.

A polypeptide and an attachment moiety with which the polypeptide will react can include components of a SpyTag/SpyCatcher system (See, Zakeri et al. *Proceedings Nat'l Acad. Sciences USA.* 109 (12): E690-7 (2012)). In this system, a 13 amino acid tag polypeptide (Spy Tag) forms a first coupling handle, with a 12.3 kDa protein (Spy-Catcher) forming the partner to the first coupling handle. Optionally, the Spy Catcher can be attached to a polypeptide. The Spy Catcher can irreversibly bond to a Spy Tag on a particle through an isopeptide bond. As will be appreciated, either the Spy Tag or the Spy Catcher can be on a particle and a polypeptide can be functionalized with the other partner.

In some configurations, an attachment moiety on a particle can be reactive in a click reaction. Attachment can be accomplished in part by chemical reaction of a click moiety with a reactive moiety on a polypeptide. The chemical conjugation may proceed via an amide formation reaction, reductive amination reaction, N-terminal modification, thiol Michael addition reaction, disulfide formation reaction, copper (I)-catalyzed alkyne-azide cycloaddition (CuAAC) reaction, strain-promoted alkyne-azide cycloaddtion reaction (SPAAC), Strain-promoted alkyne-nitrone cycloaddition (SPANC), inverse electron-demand Diels-Alder (IEDDA) reaction, oxime/hydrazone formation reaction, free-radical polymerization reaction, or a combination thereof.

Moieties that participate in cycloaddition reactions may be utilized to attach a polypeptide, or fragment thereof, to a particle. In cycloaddition reactions, two or more unsaturated moieties form a cyclic product with a reduction in the degree of unsaturation, these reaction partners are typically absent from natural systems, and so the use of cycloadditions for conjugation utilizes the introduction of unnatural functionality within a coupling partner. Exemplary moieties and their attachment reactions include:

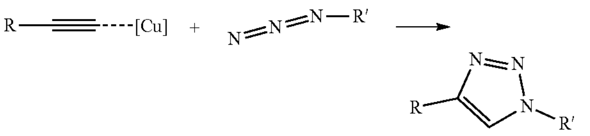

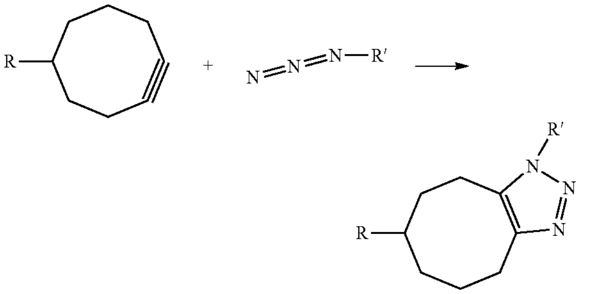

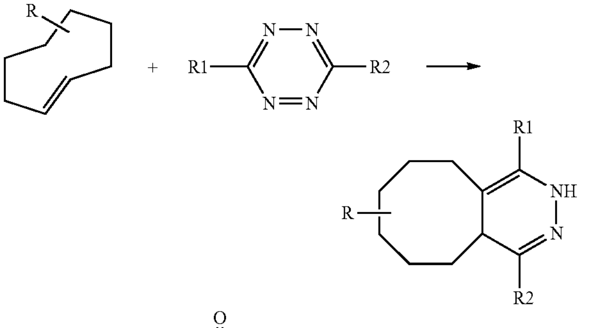

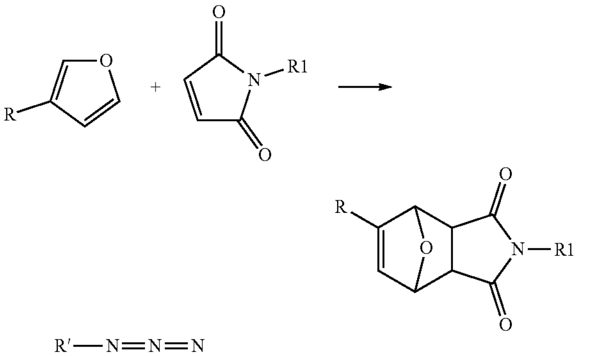

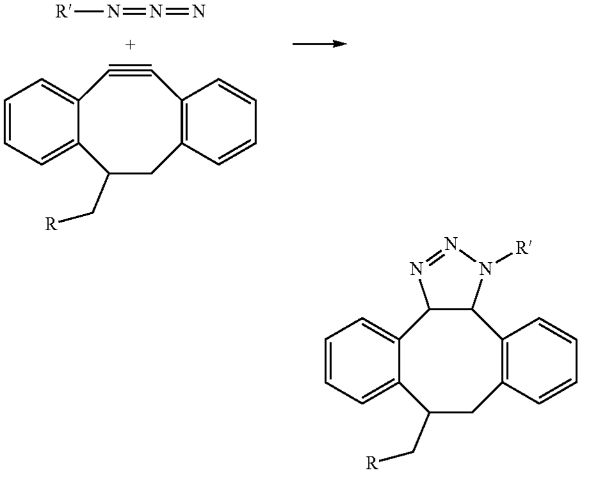

In some cases, moieties that participate in Copper-Catalyzed Azide-Alkyne Cycloadditions (CuAAC) may be utilized to attach a polypeptide to a particle. Optionally, moieties that participate in Strain-Promoted Azide-Alkyne Cycloadditions (SPAAC) may be utilized. One of an azide or alkyne can be connected to a polypeptide and reacted with a particle connected to the other. A CuAAC or SPAAC reaction can be performed to produce a triazole attachment of a polypeptide to a particle.

Moieties that participate in inverse-electron demand Diels-Alder (IEDDA) reactions may be utilized to attach a polypeptide to a particle. One of a 1,2,4,5-tetrazine moiety, strained alkene moiety or strained alkyne can be connected to an antibody conjugate and, optionally, subjected to an IEDDA reaction. Exemplary moieties include, but are not limited to, trans-cyclooctenes, functionalized norbornene derivatives, triazines, or spirohexene. In some cases, a maleimide or furan can be used as an attachment moiety and, optionally, used in a hetero-Diels-Alder cycloaddition between a maleimide and furan. In some cases, a Diels-Alder reaction can achieve covalent coupling of a diene moiety with an alkene moiety to form a six-membered ring complex for attachment.

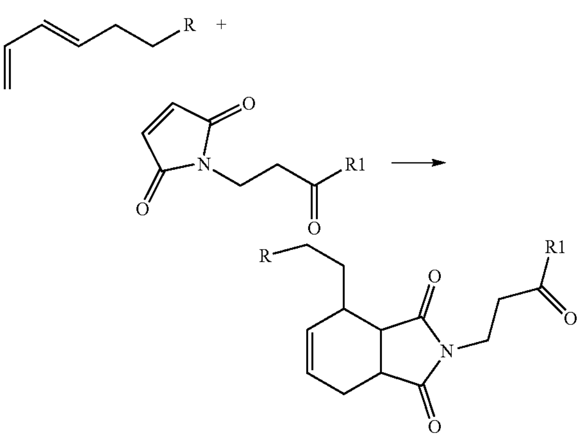

Amines can be used in a variety of attachment reactions. For example, an amine can react with an aldehyde via reductive amination to form an amine attachment. An isothiocyanate moiety may react with an amine to form a thiourea bond.

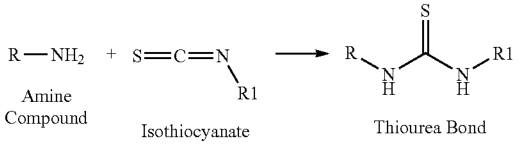

An isocyanate moiety can react with an amine moiety to form an isourea bond.

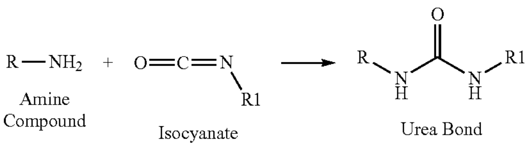

An acyl azide moiety can react with a primary amine to form an amide bond.

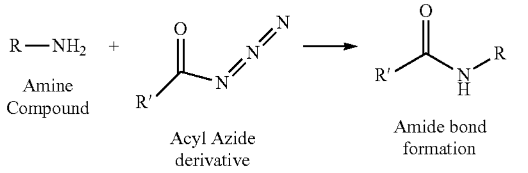

An N-hydroxysuccinimide (NHS) ester moiety can react with an amine moiety to form an amide bond.

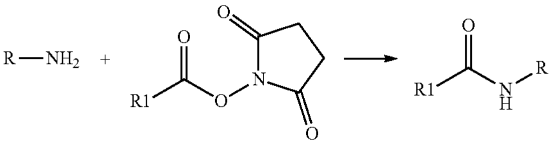

A sulfonyl chloride moiety can react with a primary amine to form a sulfonamide linkage.

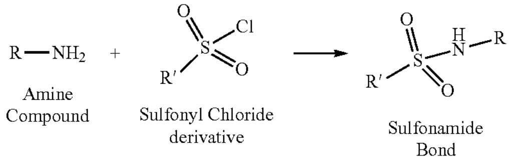

An aryl halide moiety, such as fluorobenzene derivative, can form a covalent bond with an amine moiety. Other nucleophiles such as thiol, imidazolyl, and phenolate groups can also react with an aryl halide to form stable bonds. As shown below, a fluorobenzene moiety can react with an amine to form a substituted aryl amine bond.

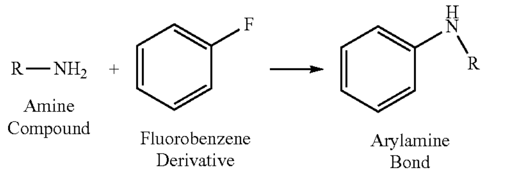

An imidoester moiety can react with an amine to form an amidine linkage.

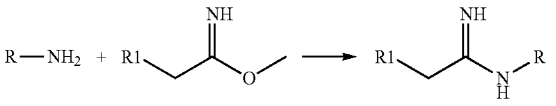

An epoxide or oxirane moiety can react with a nucleophile in a ring-opening process. The reaction can take place with primary amines, sulfhydryls, or hydroxyl groups to create secondary amine, thioether, or ether bonds, respectively.

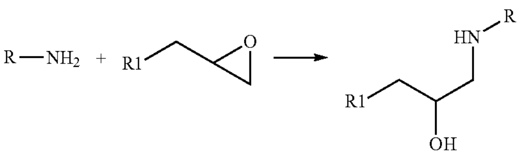

A carbonate moiety can react with a nucleophile to form a carbamate linkage.

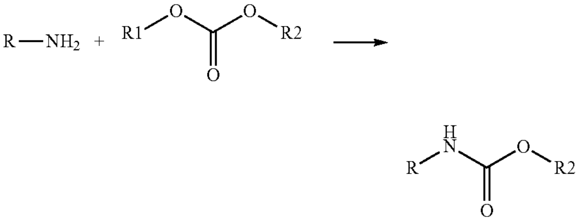

A carbonyl moiety, such as an aldehyde, ketone, or glyoxal, can react with an amine to form a Schiff base intermediate. In some cases, the addition of sodium borohydride or sodium cyanoborohydride will result in reduction of the Schiff base intermediate and covalent bond formation, creating a secondary amine bond.

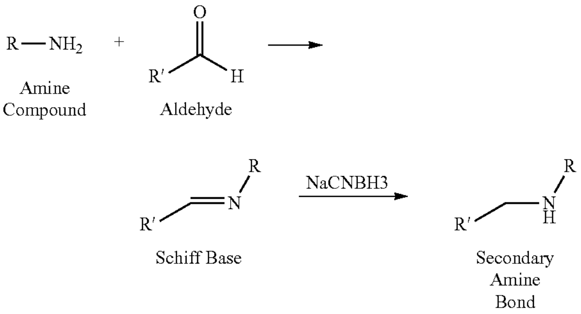

A carboxylate moiety can be used for attachment. For example, diazomethane and other diazoalkyl derivatives may be reacted with carboxylate groups. In some cases, N,N'-Carbonyl diimidazole (CDI) may be used to react with a carboxylate to form N-acylimidazole which can then react with an amine to form an amide bond or with a hydroxyl to form an ester linkage.

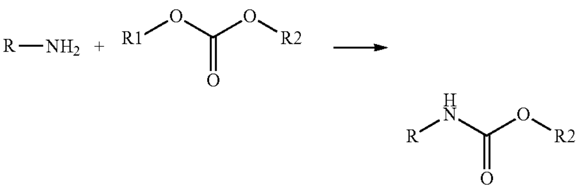

N,N'-disuccinimidyl carbonate moieties and N-hydroxysuccinimidyl chloroformate moieties are reactive toward nucleophiles. These moieties can react with amines or hydroxyls to form stable crosslinked products.

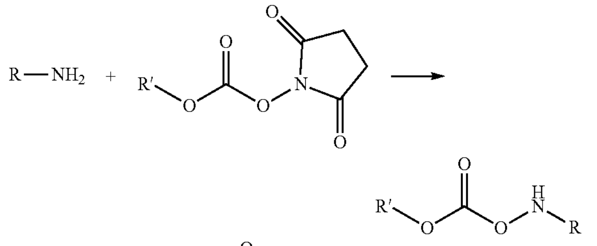

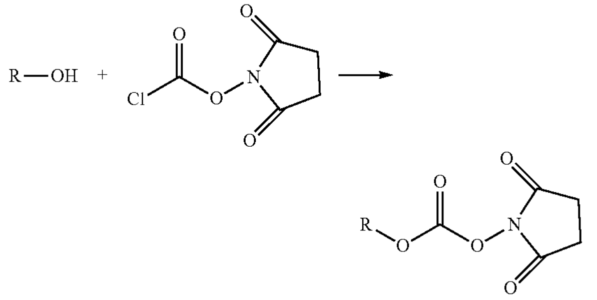

A fluorophenyl ester moiety can react with an amine to form an amide bond. Exemplary fluorophenyl esters include pentafluorophenyl (PFP) ester, tetrafluorophenyl (TFP) ester, or sulfo-tetrafluoro-phenyl (STP) ester.

A tosylate ester can be used as an attachment moiety. For example, a tosylate ester can be formed from reaction of 4-toluenesulfonyl chloride (also called tosyl chloride or TsCl) with a hydroxyl moiety to yield a sulfonyl ester derivative. The sulfonyl ester can couple with a nucleophile to produce a covalent bond, for example, producing a secondary amine linkage with a primary amine, a thioether linkage with a sulfhydryl, or an ether bond with a hydroxyl.

Carbodiimide chemistry can be useful. Generally, carbodiimides are zero-length crosslinking agents that may be used to mediate the formation of an amide or phosphoramidate linkage between a carboxylate and an amine or between a phosphate and an amine, respectively. Accordingly, an amine, carboxylate, or phosphate can be used as an attachment moiety of a particle or reactive moiety of a polypeptide.

A hydroxymethyl phosphine moiety may be useful. For example, tris(hydroxymethyl) phosphine (THP) and β-[tris (hydroxymethyl)phosphino] propionic acid (THPP) can react with nucleophiles, such as amines, to form covalent linkages.

An aldehyde or ketone moiety can be useful. For example, derivatives of hydrazine, especially the hydrazide compounds formed from carboxylate groups, can react with aldehyde or ketone moieties. In some cases, a carboxylate moiety can be used as an attachment moiety or reactive moiety.

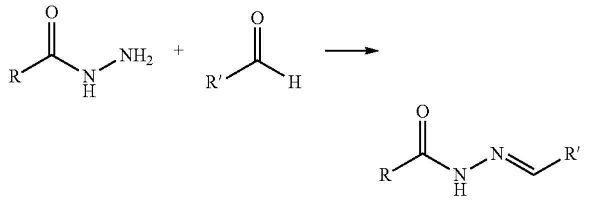

An aminooxy can be utilized to attach a polypeptide to a particle. For example, reaction can occur between an aldehyde and an aminooxy to yield an oxime linkage (aldoxime). This reaction is also quite efficient with ketones to form an oxime called a ketoxime. Accordingly, an aldehyde or ketone moiety can be used.

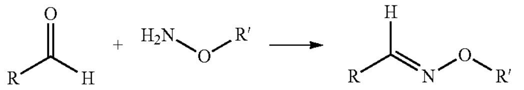

An attachment moiety or reactive moiety can be photoreactive. For example, an aryl azide or halogenated aryl azide can be used. Their photoreactions are orthogonal to photo thiol-yne reactions because they are known to occur only under conditions much harsher than photo thiol-yne conditions such as by irradiation at short wavelength ultraviolet (UVC) for an extended period.

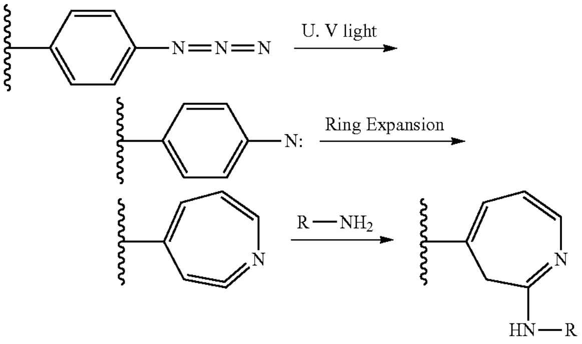

Other photoreactive moieties are orthogonal to photo thiol-yne reactions and can be useful such as benzophenone.

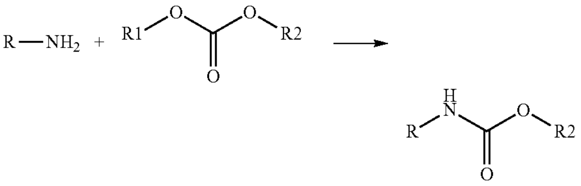

Further examples of useful photoreactive moieties include, for example, anthraquinone, alkyne, alkene, propargyl-ether, or propargyl-amine. Photocages can also be used as attachment moieties. Exemplary photocages are based around o-nitrobenzyl and coumarin chromophores. Photoaffinity moieties can be utilized and can achieve attachment via light induced formation of highly reactive intermediates, which then react with the nearest accessible functional group with high spatial precision. Examples include phenylazides, benzophenones, and phenyl-diazirines.

Activated halogen derivatives can be used to create sulfhydryl-reactive moieties such as haloacetyl, benzyl halides, and alkyl halides. In each of these compounds, the halogen group may be easily displaced by an attacking nucleophilic substance to form an alkylated derivative, such as the thioether bond resulting from reaction of a sulfhydryl with an iodoacetyl derivative as shown below.

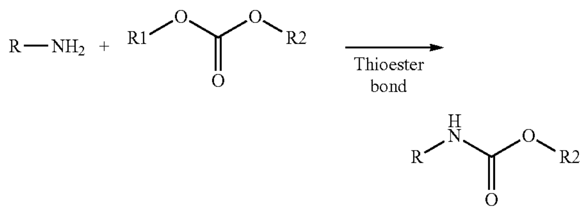

A maleimide moiety can undergo an alkylation reaction with a sulfhydryl to form a stable thioether bond.

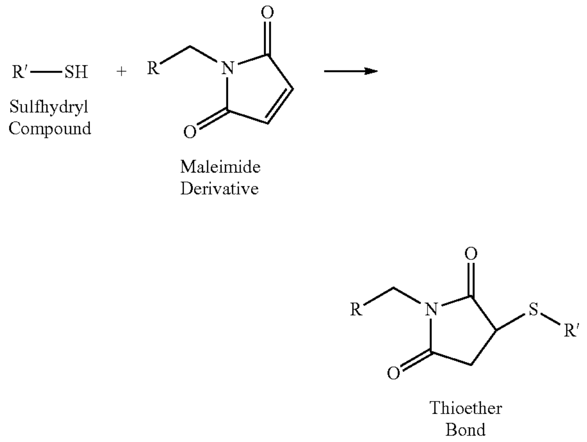

An aziridine moiety can react with nucleophiles. For example, a sulfhydryls can react with aziridine moiety to form a thioether bond.

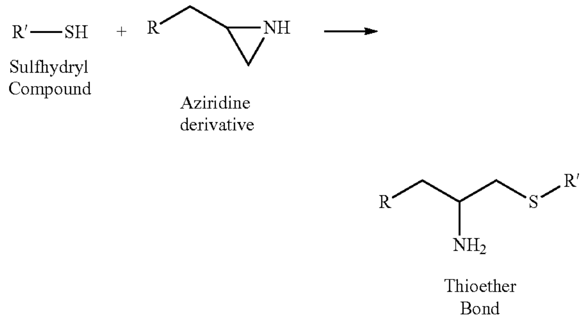

An acryloyl moiety can react with a sulfhydryl to form a thioether bond.

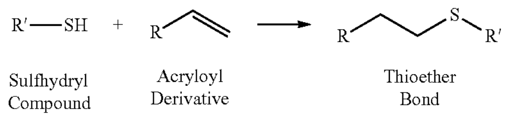

An electron-deficient aryl moiety can react with a sulfhydryl to form a substituted aryl bond.

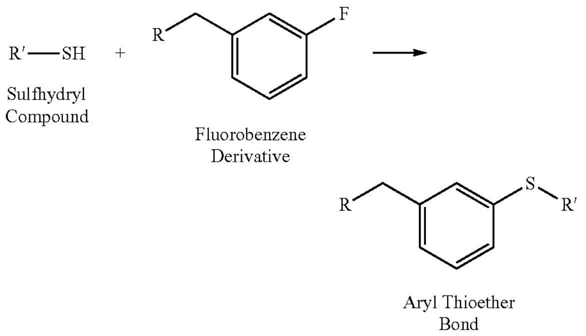

A pyridyl dithiol moiety can undergo an interchange reaction with a free sulfhydryl to yield a mixed disulfide product.

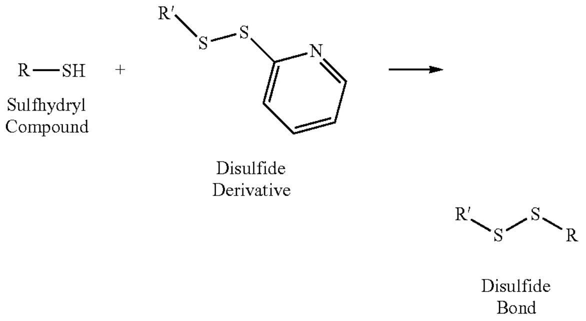

A vinyl sulfone moiety can react with thiols, amines and hydroxyls. The product of the reaction of a thiol with a vinyl sulfone gives a beta-thiosulfonyl linkage.

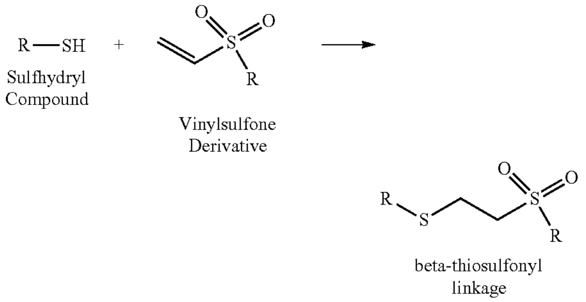

A polypeptide can be attached to a particle via binding moieties having affinity for each other. For example, a polypeptide can include a first binding moiety that binds to a second binding moiety on a particle. A first binding moiety may bind with a second binding moiety in a non-covalent manner. Some binding moieties can also be chemically reactive or catalytic (e.g., kinases, proteases, etc.). A binding moiety can be chemically non-reactive and non-catalytic, thereby not permanently altering the chemical structure of another binding moiety to which it binds. Exemplary pairs of binding moieties include, but are not limited to, an antibody, such as a full-length antibody or functional fragment thereof which bind to epitopes. Other useful binding moiety pairs include, for example, (strept) avidin (or analogs thereof) and biotin (or analogs thereof), complementary nucleic acids, nucleic acid aptamers and their ligands, lectins and carbohydrates or the like.

A particle can be attached to a polypeptide via one or more linkage. For example, a polypeptide can have at least 1, 2, 5, 10, 20, 30, 40, 50, 75, 100 or more linkages to particle. Alternatively or additionally, a polypeptide can have at most 100, 75, 50, 40, 30, 20, 10, 5, 2, or 1 linkages to particle. A plurality of immobilized polypeptides, for example, produced or manipulated in a method set forth herein, can include an average number of linkages in one or more of the above ranges.

The type of amino acids of a polypeptide that are linked to a particle will depend on the attachment chemistry used. For example, a particle can be linked to a polypeptide via at least 50%, 75%, 90%, 95% or more of the amino acids of a given type in the polypeptide. Alternatively, a particle can be linked to a polypeptide via at most 95%, 90%, 75%, 50% or less of the amino acids of a given type in the polypeptide. The given type of amino acid can be one of a lysine, histidine, arginine, cysteine, methionine, aspartic acid, glutamic acid, serine, threonine, tyrosine, glutamine or asparagine.

Figure 2:
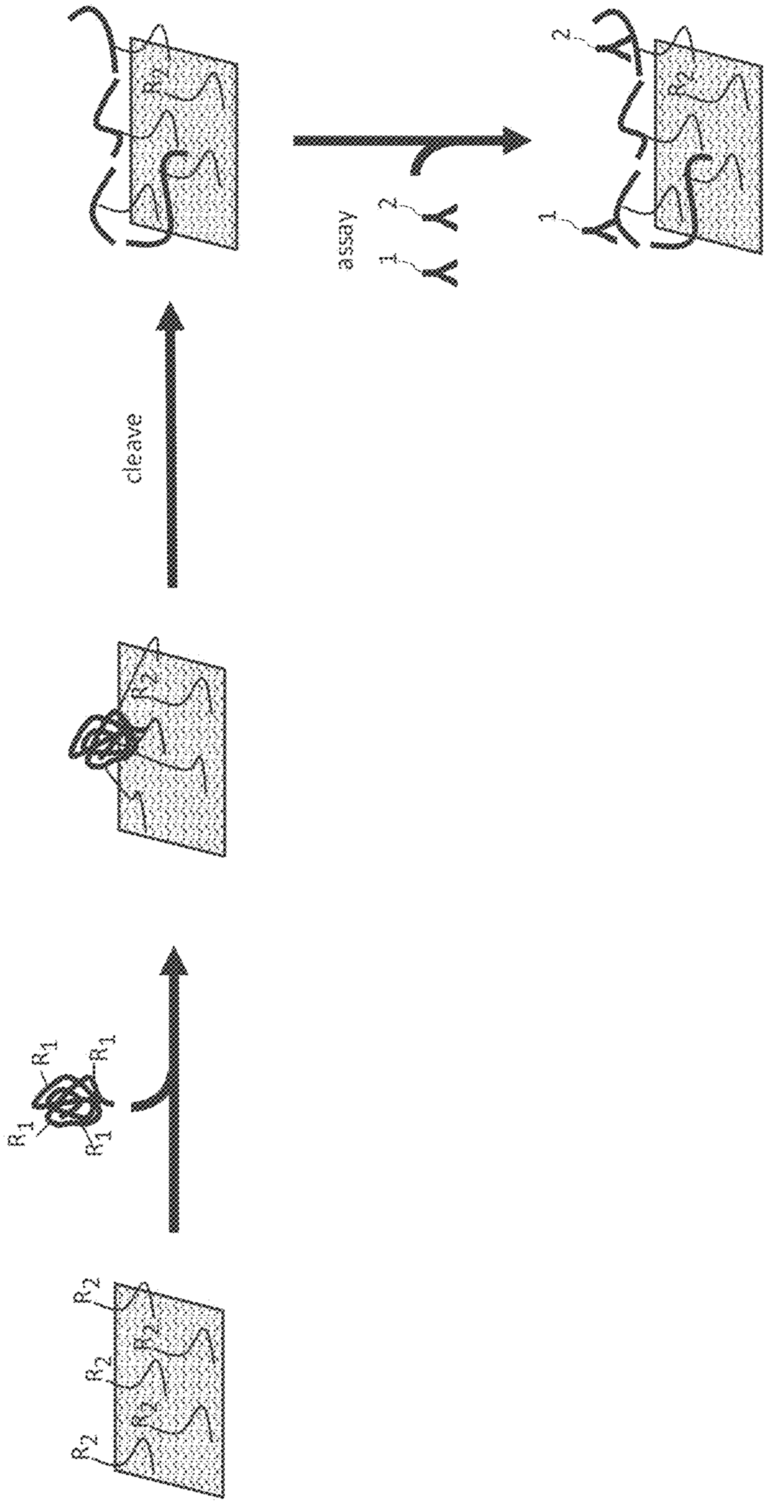
FIG. 2 shows a diagram of a process for attaching a polypeptide (shown as a globular squiggle) with first reactive moieties ($R_1$) to a particle (shown as a rectangle) having a plurality of second reactive moieties ($R_2$) to form an immobilized polypeptide, cleaving the immobilized polypeptide to produce an immobilized set of polypeptide fragments and detecting the immobilized set of polypeptide fragments.

In some configurations of the methods set forth herein, a step of attaching a polypeptide to a particle can be carried out by contacting a particle having a plurality of attachment moieties with a polypeptide having a plurality of amino acids that are reactive with the attachment moieties. The plurality of attachment moieties on the particle can react with the plurality amino acids of the polypeptide to form a plurality of linkages. As such, a plurality of amino acids of a polypeptide can react with a plurality of attachment moieties on a particle in a single step, thereby producing an immobilized polypeptide having a plurality of amino acids linked to the particle. An exemplary method is diagrammed in FIG. 2. In the first step a polypeptide (shown as a globular squiggle) having a plurality of first reactive moieties ($R_1$) is contacted with a particle (shown as a rectangle) having a plurality of second reactive moieties ($R_2$). The second reactive moieties are optionally attached to the particle via linkers (shown as S-shaped lines). Reaction between the first and second reactive moieties creates a plurality of linkages (e.g. covalent or non-covalent linkages) between the particle and the polypeptide, thereby producing an immobilized polypeptide. The immobilized polypeptide is then cleaved, for example, using one or more type of protease, to produce an immobilized set of polypeptide fragments. The immobilized set of fragments is then contacted with two affinity reagents in a binding assay.

In other configurations of the methods set forth herein, attaching a polypeptide to a particle can be carried out in two or more steps. For example, a step of attaching a polypeptide to a particle can include (i) reacting a first attachment moiety on a particle with a polypeptide, thereby producing an attached polypeptide, and then (ii) forming a plurality of linkages between amino acids of the attached polypeptide and the particle. An advantage of using two or more steps to attach a polypeptide to a particle is the ability to produce a particle having a single polypeptide (i.e. one, and only one, polypeptide) attached thereto. This can be useful, for example, in multiplex configurations where a plurality of particles is contacted with a plurality of polypeptides such that a given particle can contact multiple polypeptides during the course of the attachment reaction and a given polypeptide can contact multiple particles during the course of the attachment reaction. Several configurations that provide this advantage are set forth below.

Figure 3:
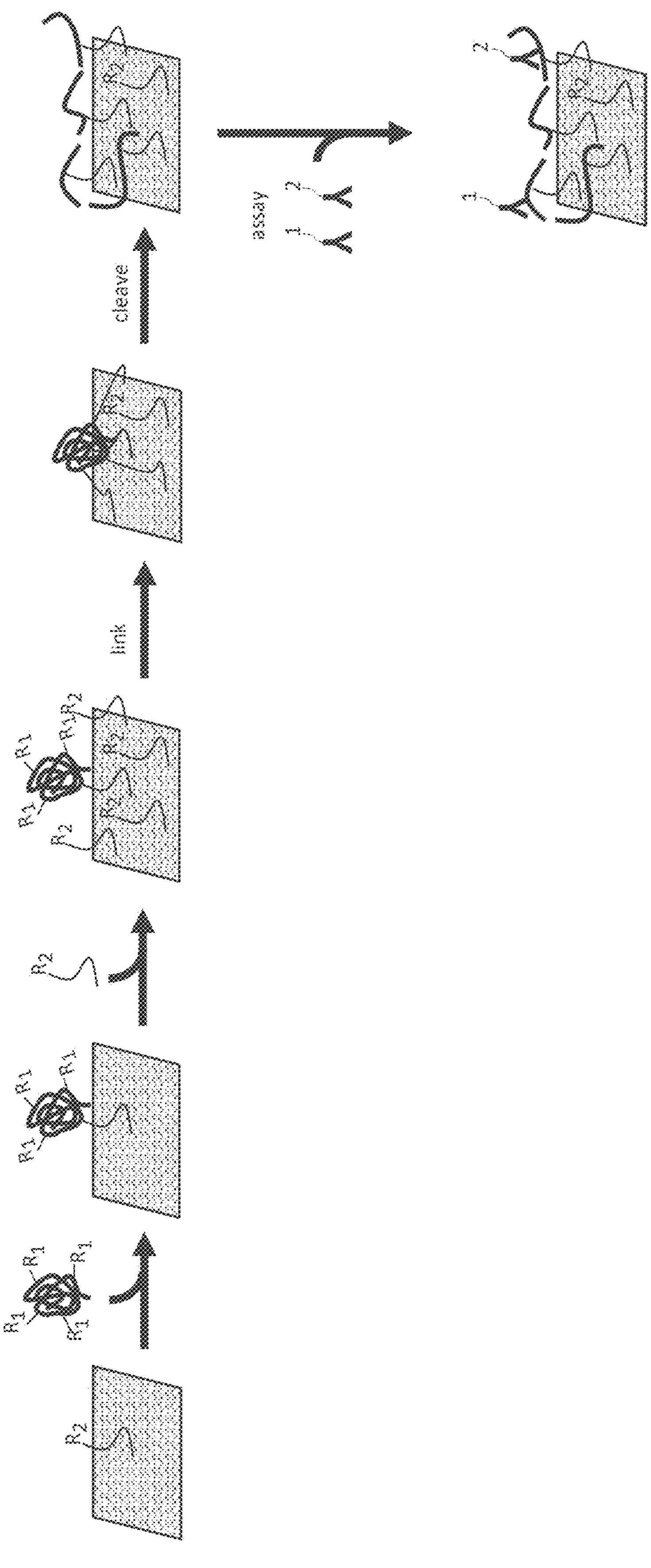
FIG. 3 shows a diagram of a process for attaching a polypeptide (shown as a globular squiggle) with first reactive moieties ($R_1$) to a particle (shown as a rectangle) having a single second attachment moiety ($R_2$) to form an immobilized polypeptide, attaching linkers to the particle, linking a plurality of amino acids of the polypeptide to the linkers, cleaving the immobilized and linked polypeptide to produce an immobilized set of polypeptide fragments and detecting the immobilized set of polypeptide fragments.

In a first configuration of the above multistep attachment process, step (i) can be carried out using a particle having only one attachment moiety that is reactive with reactive moieties on the polypeptide. As such, whether the polypeptide has only a single reactive amino acid or multiple reactive amino acids, only one amino acid can form a linkage with the particle. In this configuration, step (ii) can be carried out by modifying the particle to include a plurality of attachment moieties that can then be reacted with reactive moieties on the polypeptide to form a plurality of linkages between amino acids of the attached polypeptide and the particle. A diagram exemplifying aspects of this configuration is shown in FIG. 3. In the first step, a polypeptide having a plurality of first reactive moieties ($R_1$) is contacted with a particle having a single second attachment moiety ($R_2$). Reaction between one of the first reactive moieties and the attachment moiety produces an immobilized polypeptide. Optionally, the second attachment moiety is tethered to the particle via a linker such that the polypeptide becomes immobilized to the particle via the linker. Then the particle is modified to attach a plurality of attachment moieties. The attachment moieties added in the second step are shown as being the same type ($R_2$) as the attachment moiety used in the first step and are tethered to the particle via linkers. It will be understood that the attachment moieties added in the second step can differ from the attachment moiety added in the first step. The added attachment moieties are then reacted with a plurality of first reactive moieties ($R_1$) on the polypeptide to form a plurality of linkages between amino acids of the polypeptide and the particle. The linked polypeptide is then cleaved, for example, using one or more type of protease, to produce an immobilized set of polypeptide fragments that is assayed by binding to two affinity reagents (labeled 1 and 2, respectively).

Figure 4:
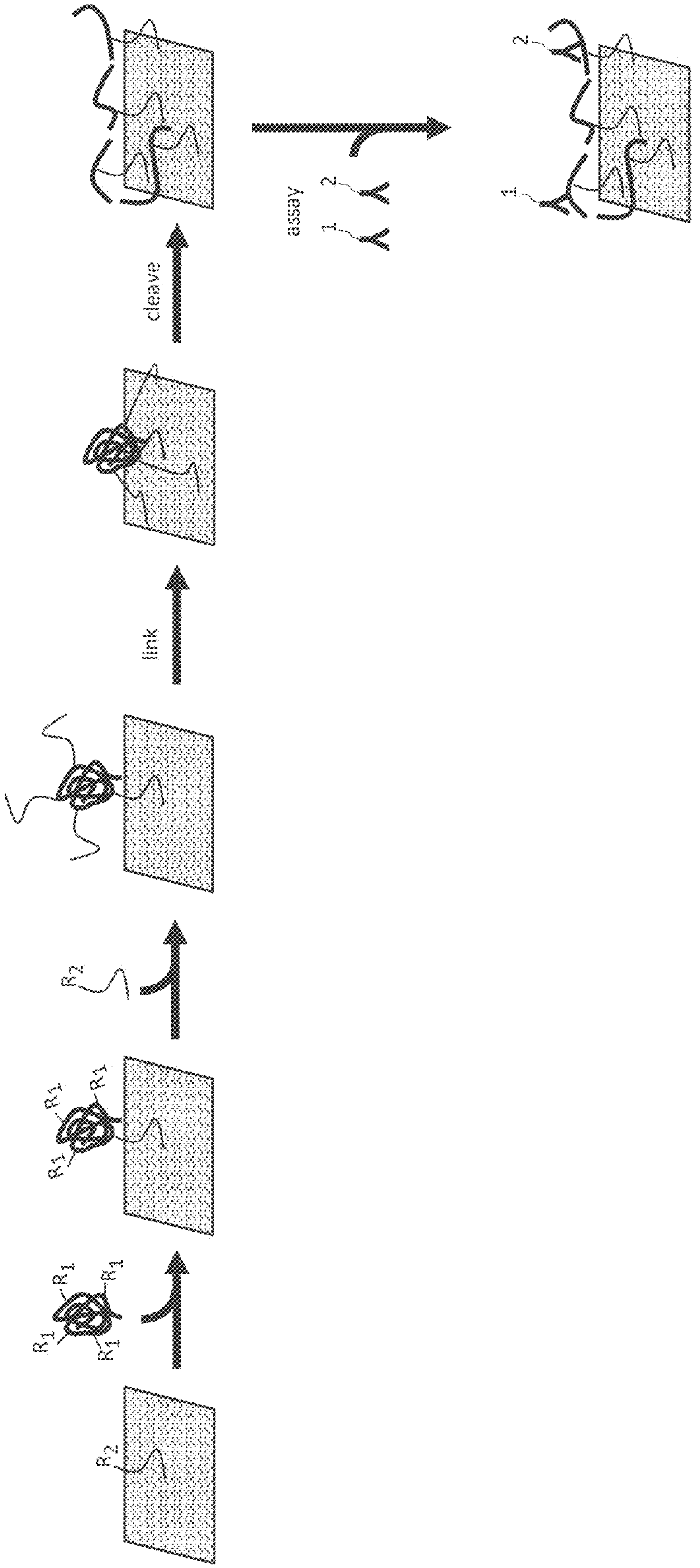
FIG. 4 shows a diagram of a process for attaching a polypeptide (shown as a globular squiggle) with first reactive moieties ($R_1$) to a particle (shown as a rectangle) having a single attachment moiety ($R_2$) to form an immobilized polypeptide, attaching linkers to amino acids of the polypeptide, linking the amino acids to the particle, cleaving the immobilized and linked polypeptide to produce an immobilized set of polypeptide fragments and detecting the immobilized set of polypeptide fragments.

In a second configuration of the above multistep attachment process, step (i) can be carried out using a particle having only one attachment moiety that is reactive with reactive moieties on the polypeptide, and step (ii) can be carried out by modifying the polypeptide to include a plurality of linker moieties that can then be attached to the particle to form a plurality of linkages between amino acids of the attached polypeptide and the particle. A diagram exemplifying aspects of this configuration is shown in FIG. 4. In the first step, a polypeptide having a plurality of first reactive moieties ($R_1$) is contacted with a particle having a single attachment moiety ($R_2$). Reaction between one of the first reactive moieties and the attachment moiety produces an immobilized polypeptide. Then a plurality of linkers is attached to the immobilized polypeptide via reaction between second reactive moieties ($R_2$) on each linker and first reactive moieties ($R_1$) on the polypeptide. The linkers are then attached to the particle to form a plurality of linkages between amino acids of the polypeptide and the particle. The linked polypeptide is then cleaved, for example, using one or more type of protease, to produce an immobilized set of polypeptide fragments that is assayed by binding to two affinity reagents (labeled 1 and 2, respectively).

Figure 5:
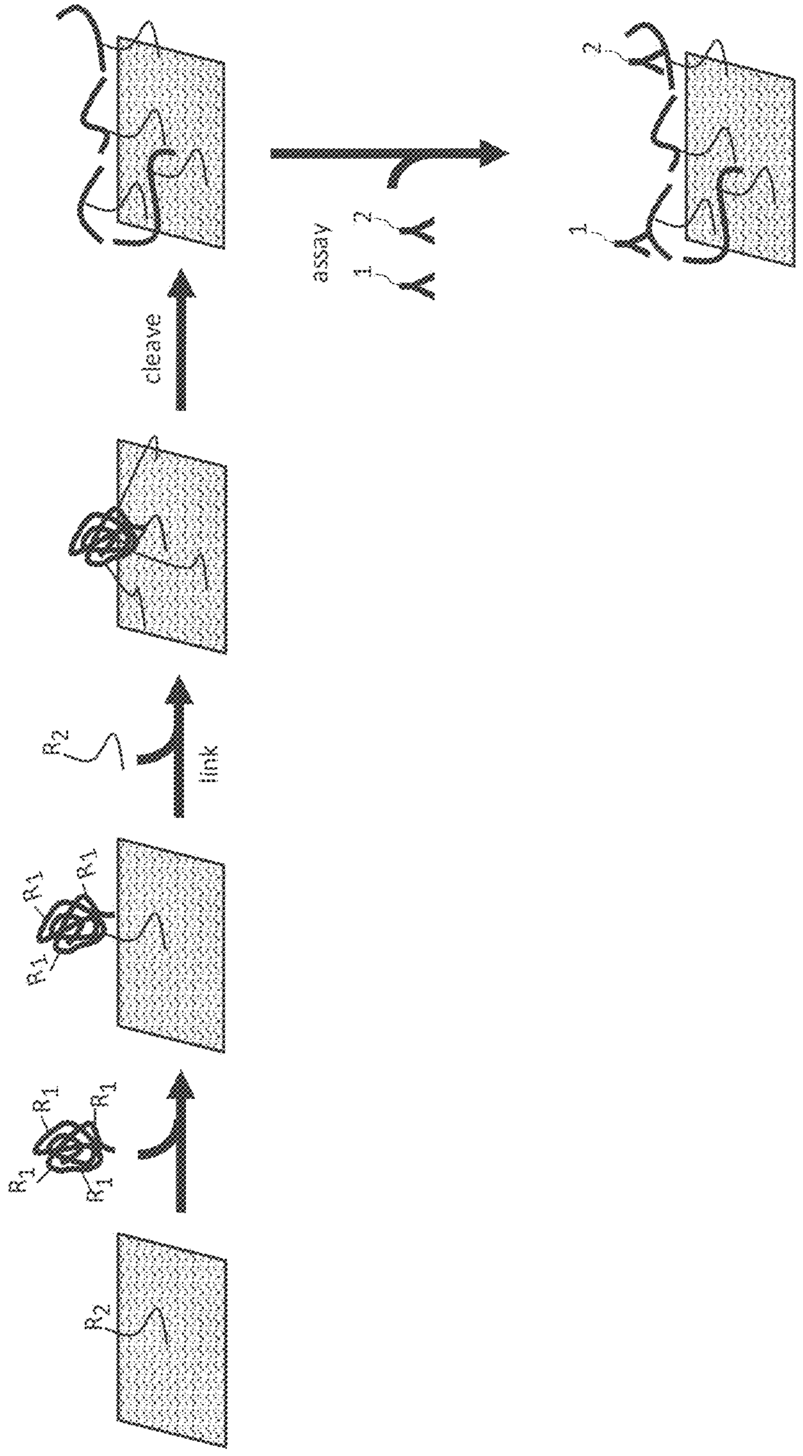
FIG. 5 shows a diagram of a process for attaching a polypeptide (shown as a globular squiggle) with first reactive moieties ($R_1$) to a particle (shown as a rectangle) having a single attachment moiety ($R_2$) to form an immobilized polypeptide, linking amino acids of the polypeptide to the particle, cleaving the immobilized and linked polypeptide to produce an immobilized set of polypeptide fragments and detecting the immobilized set of polypeptide fragments.

In a third configuration of the above multistep attachment process, step (i) can be carried out using a particle having only one attachment moiety that is reactive with reactive moieties on the polypeptide, and step (ii) can be carried out by contacting the immobilized polypeptide with linkers that react with a plurality of first reactive moieties on the polypeptide and with the particle to form a plurality of linkages between amino acids of the attached polypeptide and the particle. A diagram exemplifying aspects of this configuration is shown in FIG. 5. In the first step, a polypeptide having a plurality of first reactive moieties ($R_1$) is contacted with a particle having a single attachment moiety ($R_2$). Reaction between one of the first reactive moieties and the attachment moiety produces an immobilized polypeptide. Then a plurality of linkers is contacted with the immobilized polypeptide under conditions wherein a second reactive moiety ($R_2$) on each linker reacts with a first reactive moiety ($R_1$) on the polypeptide and wherein the linkers attach to the particle. The linked polypeptide is then cleaved, for example, using one or more type of protease, to produce an immobilized set of polypeptide fragments that is assayed by binding to two affinity reagents (labeled 1 and 2, respectively).

Figure 6:
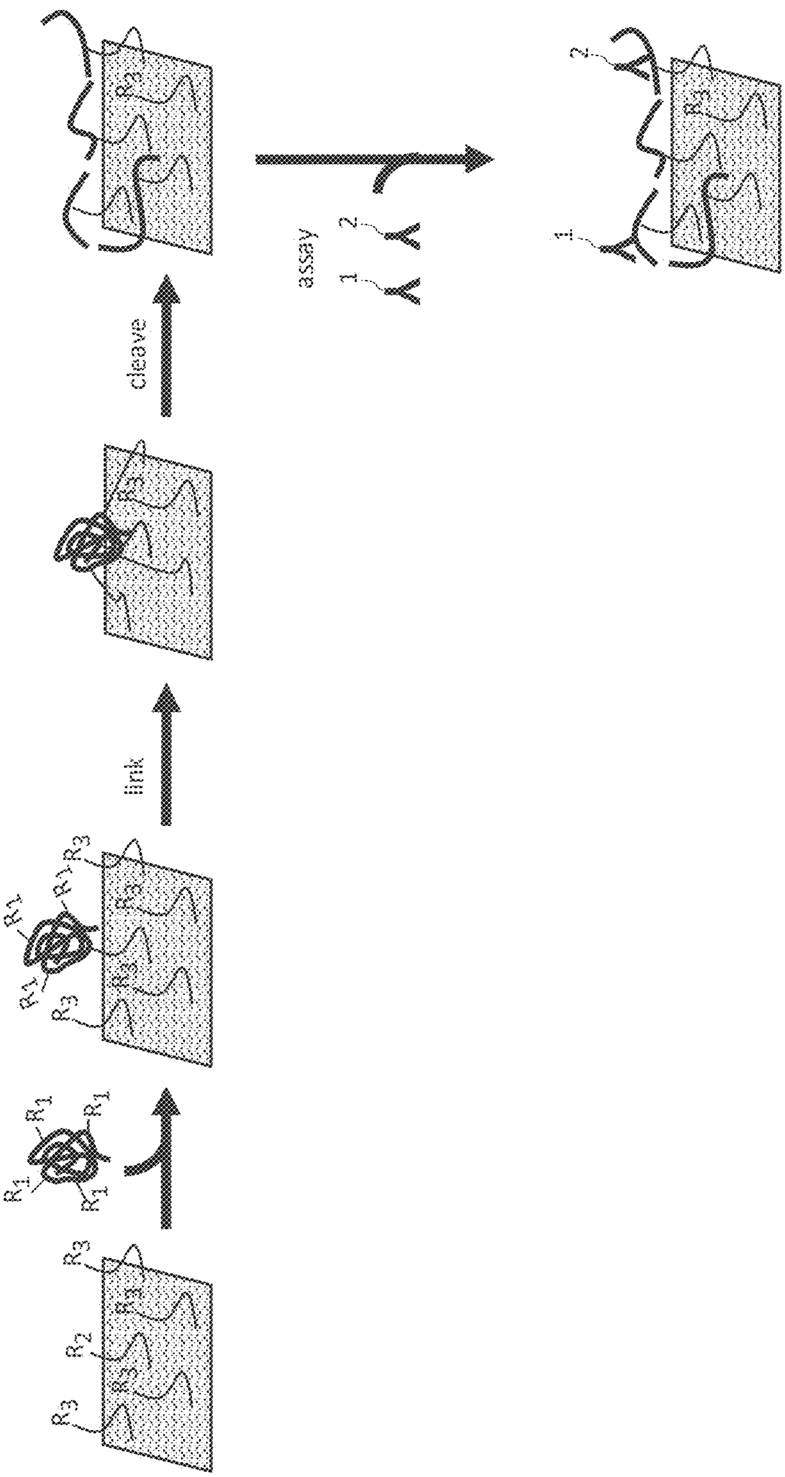
FIG. 6 shows a diagram of a process for attaching a polypeptide (shown as a globular squiggle) with first reactive moieties ($R_1$) to a particle (shown as a rectangle) having a single attachment moiety ($R_2$) at first and then to a plurality of second attachment moieties ($R_3$), to form an immobilized polypeptide, linking a plurality of amino acids of the polypeptide to linkers on the particle, cleaving the immobilized and linked polypeptide to produce an immobilized set of polypeptide fragments and detecting the immobilized set of polypeptide fragments.

In a fourth configuration of the above multistep attachment process, step (i) can be carried out using a particle having a single attachment moiety of a first type, the first type of attachment moiety reacting with the polypeptide to form an attachment. The particle can also include a plurality of attachment moieties of a second type. The first type of attachment moiety can be orthogonal to the attachment moieties of the second type, such that the second type of attachment moiety does not react with amino acids of the polypeptide during step (i). In this case, step (ii) can employ reaction conditions that differ from those of step (i), such that reaction can occur between the amino acids of the polypeptide and the attachment moieties of the second type. A diagram exemplifying aspects of this configuration is shown in FIG. 6. In the first step a polypeptide having a plurality of first reactive moieties ($R_1$) is contacted with a particle having a single attachment moiety ($R_2$) of a first type. A first reaction occurs under conditions in which one of the first reactive moieties forms a bond to the attachment moiety to produce an immobilized polypeptide. The immobilized polypeptide is then subjected to a second reaction in which a plurality of second attachment moieties ($R_3$) on the particle attach to a plurality of the first reactive moieties ($R_1$) on the polypeptide. The linked polypeptide is then cleaved, for example, using one or more type of protease, to produce an immobilized set of polypeptide fragments that is assayed by binding to two affinity reagents (labeled 1 and 2, respectively).

Linkers used in a method or composition of the present disclosure can be relatively flexible or relatively rigid. Flexibility of a linker can provide a large degree of freedom for positioning of a moiety that is attached to the linker. For example, attachment moieties that are attached to particles via flexible linkers can readily interact with a polypeptide that is also attached to the particle. Accordingly, the linkers can be attached to the particles at a wide variety of locations relative to the point of attachment for the polypeptide. Rigid linkers can be useful for reducing the degrees of freedom for positioning moieties that are attached to the linkers. For example, polypeptide fragments can be attached to rigid linkers to inhibit the fragments from interacting with each other. This can increase accessibility of the fragments to affinity reagents during a binding assay.

Linker flexibility can be altered in the course of a method set forth herein. For example, linkers can be in a relatively flexible state when bearing unreacted attachment moieties. As such, the linkers can be in a flexible state during steps that are carried out to link a particle to a plurality of amino acids of a polypeptide. The linkers can be converted to a relatively rigid, for example, when the linkers are attached to polypeptide fragments. As such, the linkers can be in a rigid state during steps carried out to detect a set of polypeptide fragments, for example, via binding to affinity reagents. Nucleic acid linkers can be particularly useful since they are relatively flexible in the single stranded state and then become more rigid when converted to a double stranded state by hybridization to a complementary nucleic acid. Accordingly, a plurality of linkers can be in a single stranded state when bearing unreacted attachment moieties and then hybridized to complementary nucleic acids such that they are in a double stranded state when bearing polypeptide fragments.

A linker can demonstrate differential flexibility in response to environmental conditions such as temperature, pH or light. For example, the flexibility of poly(N-isopropylacrylamide) (PNIPA) and various co-polymers thereof are temperature or pH responsive. See, for example, Schild *Progress in Polymer Science.* 17 (2): 163-249 (1992) and Okano et al., *Journal of Controlled Release.* 11 (1-3): 255-265 (1990), each of which is incorporated herein by reference. Exemplary light responsive polymers include, but are not limited to, those having azobenzene, stilbene, cyanostilbene, stiff-stilbene, diarylethene, spiropyrans, hydrozones, orthonitrobenzyl moieties, triarylamine or cinnamic acid derivatives. See, for example, Xu and Feringa *Adv. Mater.* 35:2204413 (2023), which is incorporated herein by reference. A light-sensitive moiety, azobenzene, can be incorporated into polyacrylamide to yield copolymers that are light responsive. See, for example, Zhao *ACS Appl. Polym. Mater.* 2:256-262 (2020), which is incorporated herein by reference.

Linker length can be altered between steps of a method set forth herein. For example, a linker can be in a relatively short conformation for one or more steps of a method set forth herein and in a relatively long conformation for one or more other steps of the method. A particularly useful linker is a nucleic acid that can be in a relatively short conformation due to an internal region of self-hybridization (e.g. a hairpin) and in a relatively long conformation when the region is not self-hybridized. Self-hybridization can be prevented, for example, by exposing the nucleic acid linker to conditions that inhibit hybridization (e.g. heat, salt or solvents that are known to inhibit nucleic acid hybridization) or by hybridizing the nucleic acid linker to a nucleic acid that is complementary to the region that would otherwise self-hybridize. Lengthening a linker can be useful for separating polypeptide fragments from each other, for example, to facilitate binding of affinity reagents.

A linker used in a method set forth herein can include a label. In some cases, a plurality of linkers can be attached to a particle, each of the linkers having a different label. As such, a particle can be attached to a polypeptide, or fragments thereof, via uniquely labeled linkers. In this example, each polypeptide fragment can be attached to a unique label. Any of a variety of labels can be used including, but not limited to, those set forth herein. A particularly useful linker is a nucleic acid having a unique nucleotide sequence. The nucleotide sequence can function as a tag that is decoded to identify the polypeptide or polypeptide fragment to which it is attached.

Nucleic acid linkers, whether or not having unique nucleotide sequences, can share a common sequence. The common sequence of a set of linkers can be useful for hybridizing to a complementary sequence of a nucleic acid that is intended to interact with the linkers. For example, the linkers, or the polypeptide fragments to which the linkers are attached, can include a first luminophore, and an affinity reagent can include a second luminophore that is capable of Forster resonance energy transfer (FRET) with the first luminophore. In this example, the second luminophore can be attached to the affinity reagent via a nucleic acid that is complementary to the common sequence of the linkers such that the first and second luminophores are positioned for efficient FRET. If desired, an affinity reagent can be attached to luminophores via a nucleic acid linker that complements a unique sequence of a nucleic acid linker on a particle. This configuration can provide added specificity within a bead since formation of a FRET pair would indicate that the affinity reagent bound to a particular polypeptide fragment on the bead and that the fragment was attached to a particular linker on the bead.

Structured nucleic acid particles have a number of properties that render them particularly useful for methods and compositions set forth herein. First, structured nucleic acid particles can be designed to have a predefined number of attachment moieties. For example, nucleic acid origami can be engineered to have a single oligonucleotide that is modified to include an attachment moiety. The position of the oligonucleotide, along with the overall shape of the origami can also be specifically engineered. Similarly, a plurality of attachment moieties can be engineered into a nucleic acid origami structure such that the number and location of the attachment moieties on the particle is predefined. A second advantage of structured nucleic acid particles is the ability to include a variety of single stranded nucleic acid regions that serve as attachment points for complementary oligonucleotides. For example, a nucleic acid origami can be designed to include a predefined number of single-stranded sequences at known locations. These sequences can serve as attachment points for hybridization of complementary oligonucleotides that are functionalized with desired moieties such as attachment moieties. These advantages can be appreciated in the context of using nucleic acid origami as the particles in FIGS. 3 through 5. In the first step of the diagrammed methods, the origami particle can include a single attachment moiety, for example, the attachment moiety being attached to an oligonucleotide that is hybridized to a predefined complementary sequence in the origami. In subsequent steps, oligonucleotides bearing further attachment moieties (or attached to a polypeptide) can be hybridized to the origami structure at predefined locations. The oligonucleotides can be configured to have a single-stranded linker region between the attachment moiety and the point of hybridization to the origami, whereby the attachment moieties have a relatively high degree of flexibility for contacting reactive moieties on the attached polypeptide. Alternatively, the oligonucleotides can be configured to have a double-stranded linker region between the attachment moiety and the point of hybridization to the origami, whereby the linkers are relatively rigid.

A method of the present disclosure can include a step of fragmenting a polypeptide to produce a set of polypeptide fragments. In some configurations, a method of the present disclosure can include a step of fragmenting a polypeptide that is attached to a particle, thereby producing a set of polypeptide fragments attached to the particle. A polypeptide can be fragmented using any of a variety of techniques including, but not limited to, treatment with a protease, chemical reagent, physical condition, or combination thereof. Proteases can digest a polypeptide into smaller polypeptide fragments or amino acids by cleaving peptide bonds. Exopeptidases can be used to cleave the bond between a terminal amino acid to form a polypeptide fragment and amino acid. Optionally, an exopeptidase can be used to serially remove a plurality of amino acids to form a shorter polypeptide fragment. Endopeptidases can be used to cleave an internal polypeptide bond to form two polypeptide fragments. Optionally, an endopeptidase or multiple different endopeptidases can be used to cleave a polypeptide at several positions to form several fragments of the polypeptide.

Particularly useful proteases act on known cleavage sites consisting of particular amino acid sequence that they will recognize and cleave in a polypeptide. Table I provides a list of proteases and their cleavage sites (see the expasy.org website of the Swiss Institute of Bioinformatics). The first column of the table includes the common name for each protease and the other columns indicate the amino acid composition of their respective cleavage sites. The nomenclature for the relative positions of residues in the polypeptide recognition site is:

Pn---P4—P3—P2—P1—//—P1′—P2′---Pm, wherein Pn indicates the portion (variable length) of the polypeptide that is on the amino terminal side of the cleavage site; wherein Pm indicates the portion (variable length) of the polypeptide that is on the carboxy terminal side of the cleavage site; wherein P1, P2, P3, P4, P1' and P2' are positions for respective amino acid residues in the cleavage site; wherein peptide bonds between position are indicated by a dash and wherein the cleavage site is indicated as "-//-." The amino acids that contribute to recognition are identified using the single amino acid code, the word "not" indicates amino acids that when present at the listed position will inhibit proteolysis, and a dash indicates a position that can have any amino acid residue.

TABLE I

| Enzyme name | P4 | P3 | P2 | P1 | P1' | P2' |
|---|---|---|---|---|---|---|
| Arg-C proteinase | — | — | — | R | — | — |
| Asp-N endopeptidase | — | — | — | — | D | — |
| BNPS-Skatole | — | — | — | W | — | — |
| Caspase 1 | F, W, Y, or L | — | H, A or T | D | not P, E, D, Q, K or R | — |
| Caspase 2 | D | V | A | D | not P, E, D, Q, K or R | — |
| Caspase 3 | D | M | Q | D | not P, E, D, Q, K or R | — |
| Caspase 4 | L | E | V | D | not P, E, D, Q, K or R | — |
| Caspase 5 | L or W | E | H | D | — | — |
| Caspase 6 | V | E | H or I | D | not P, E, D, Q, K or R | — |

TABLE I-continued

| Enzyme name | P4 | P3 | P2 | P1 | P1' | P2' |
|---|---|---|---|---|---|---|
| Caspase 7 | D | E | V | D | not P, E, D, Q, K or R | — |
| Caspase 8 | I or L | E | T | D | not P, E, D, Q, K or R | — |
| Caspase 9 | L | E | H | D | — | — |
| Caspase 10 | I | E | A | D | — | — |
| Chymotrypsin-high specificity (C-term to [FYW], not before P) | — | — | — | F or Y | not P | — |
| | — | — | — | W | not M or P | — |
| Chymotrypsin-low specificity (C-term to [FYWML], not before P) | — | — | — | F, L or Y | not P | — |
| | — | — | — | W | not M or P | — |
| | — | — | — | M | not P or Y | — |
| | — | — | — | H | not D, M, P or W | — |
| Clostripain (Clostridiopeptidase B) | — | — | — | R | — | — |
| CNBr | — | — | — | M | — | — |
| Enterokinase | D or E | D or E | D or E | K | — | — |
| Factor Xa | A, F, G, I, L, T, V or M | D or E | G | R | — | — |
| Formic acid | — | — | — | D | — | — |
| Glutamyl endopeptidase | — | — | — | E | — | — |
| GranzymeB | I | E | P | D | — | — |
| Hydroxylamine | — | — | — | N | G | — |
| Iodosobenzoic acid | — | — | — | W | — | — |
| LysC | — | — | — | K | — | — |
| Neutrophil elastase | — | — | — | A or V | — | — |
| NTCB (2-nitro-5-thiocyanobenzoic acid) | — | — | — | — | C | — |
| Pepsin (pH 1.3) | — | not H, K, or R | not P | not R | For L | not P |
| | — | not H, K, or R | not P | F or L | — | not P |
| Pepsin (pH >2) | — | not H, K or R | not P | not R | F, L, W or Y | not P |
| | — | not H, K or R | not P | F, L, W or Y | — | not P |
| Proline-endopeptidase | — | — | H, K or R | P | not P | — |
| Proteinase K | — | — | — | A, E, F, I, L, T, V, W or Y | — | — |
| Staphylococcal peptidase I | — | — | not E | E | — | — |
| Thermolysin | — | — | — | not D or E | A, F, I, L, M or V | — |
| Thrombin | — | — | G | R | G | — |
| | A, F, G, I, L, T, V or M | A, F, G, I, L, T V, W or A | P | R | not D or E | not DE |
| Trypsin | — | — | — | K or R | not P | — |
| | — | — | W | K | P | — |
| | — | — | M | R | P | — |

A polypeptide can be digested using chemical reagents. For example, cyanogen bromide (CNBr) can be used to cleave at methionine (Met) residues; 2-(2-nitrophenyl)-3-methyl-3-bromoindolenine (BNPS-skatole) can cleave at tryptophan (Trp) residues; formic acid can cleave aspartic acid-proline (Asp-Pro) peptide bonds; hydroxylamine can cleave asparagine-glycine (Asn-Gly) peptide bonds, and 2-nitro-5-thiocyanobenzoic acid (NTCB) can cleave at cysteine (Cys) residues. Chemical reagents that are not highly site selective can also be used to randomly generate polypeptide fragments including, for example, 6M HCl or reagents used in Edman-type degradation processes. Physical digestion of polypeptides can be achieved using physical shearing, UV light, or radicals generated from interaction of light with radical forming species such as titanium dioxide.

A combination of different digestion reagents and/or conditions can be used, for example, to influence the properties of the polypeptide fragments produced. For example, a plurality of proteases can be used to digest a polypeptide. A plurality of proteases can be in simultaneous contact with one or more polypeptides, for example, being delivered as a protease cocktail. Alternatively, individual proteases of a plurality of proteases can be delivered serially. If desired, a combination of protease(s), chemical reagent(s) and/or physical conditions can be used.

One or more fragments of a polypeptide can each include at least 10, 25, 50, 100, 150, 200, 250, 500 or more amino acids. Alternatively or additionally, one or more fragments of a polypeptide can each include at most 500, 250, 200, 150, 100, 50, 25, 10 or fewer amino acids. A set of polypeptide fragments, for example, made or used in a method set forth herein, can have an average length of at least 10, 25, 50, 100, 150, 200, 250, 500 or more amino acids. Alternatively or additionally, a set of polypeptide fragments can have an average length of at most 500, 250, 200, 150, 100, 50, 25, 10 or fewer amino acids. One or all of the polypeptide fragments in a set of polypeptide fragments, for example, made or used in a method set forth herein, can have a minimum length of at least 10, 25, 50, 100, 150, 200, 250, 500 or more amino acids. Alternatively or additionally, one or all of the polypeptide fragments in a set of polypeptide fragments can have a maximum length of at most 500, 250, 200, 150, 100, 50, 25, 10 or fewer amino acids.

A set of polypeptide fragments from a given polypeptide, for example, a set produced in a method set forth herein, can include at least 2, 3, 4, 5, 6, 7, 8, 9, 10, 15, 20, 25, 50 or more fragments of the given polypeptide. Alternatively or additionally, a set of polypeptide fragments from a given polypeptide can include at most 50, 25, 20, 15, 10, 9, 8, 7, 6, 5, 4, 3, or 2 fragments of the given polypeptide. For configurations that include a plurality of polypeptide fragment sets, the sets can each include an average of at least 2, 3, 4, 5, 6, 7, 8, 9, 10, 15, 20, 25, 50 or more fragments. Alternatively or additionally, the sets of polypeptide fragments can include an average of at most 50, 25, 20, 15, 10, 9, 8, 7, 6, 5, 4, 3, or 2 peptide fragments.

A method of the present disclosure can be configured to cleave a plurality of polypeptides, whereby one or more fragments is produced from each polypeptide of the plurality. An immobilized set of polypeptide fragments can include fragments that are attached to a particle via one or more different types of amino acids. For example, a particle can be attached to one or more polypeptide fragments via (A) an amine that is present in the side chain of a lysine, histidine or arginine; (B) a sulfur that is present in the side chain of a cysteine or methionine; (C) a carboxylate that is present in the side chain of an aspartic acid or glutamic acid; (D) an oxygen that is present in the side chain of a serine, threonine or tyrosine; or (E) an amide that is present in the side chain of a glutamine or asparagine. A set of polypeptide fragments can be linked to a particle via a single type of amino acid linkage, or via two or more types of amino acid linkages. An individual fragment can be linked to a particle via a single type of amino acid linkage, or via two or more types of amino acid linkages. Optionally, an individual fragment can be linked to a particle via a single amino acid, or via multiple amino acids (e.g. multiple amino acids of a single type or multiple types of amino acids).

An immobilized set of polypeptide fragments, for example, made or used by a method set forth herein, can include substantially all the amino acid content of the polypeptide from which it was derived or a portion of the amino acid content. For example, the combined mass of a set of fragments that is attached to a particle can include at least 50%, 60%, 70%, 80%, 90%, 95% or more of the mass of the polypeptide from which the fragments were obtained. Alternatively or additionally, the combined mass of a set of fragments that is attached to a particle can include at most 95%, 90%, 80%, 70%, 60%, 50% or less of the mass of the polypeptide from which the fragments were obtained.

An immobilized set of polypeptide fragments, for example, made or used by a method set forth herein, can include substantially all the amino acid sequence content of the polypeptide from which it was derived or a portion of the sequence content. For example, the combined amino acid sequence content of a set of fragments that is attached to a particle can include at least 50%, 60%, 70%, 80%, 90%, 95% or more of the amino acid sequence of the polypeptide from which the fragments were obtained. Alternatively or additionally, the combined amino acid sequence content of a set of fragments that is attached to a particle can include at most 95%, 90%, 80%, 70%, 60%, 50% or less of the amino acid sequence of the polypeptide from which the fragments were obtained.

In some cases, fragmentation of a particle-attached polypeptide can produce one or more fragments that are not linked to the particle. For example, a polypeptide may be linked to a particle via amino acids of a particular type (e.g. lysines) and that type of amino acid may not be present in one or more fragments produced by cleavage of the polypeptide. In some cases, the type of amino acid that links the polypeptide to the particle may be present in a given fragment, but because the amino acid did not participate in forming a linkage, the fragment will not be attached to the particle. A method of the present disclosure can include a step of separating non-linked fragments of a polypeptide from a particle that is linked to other fragments of the polypeptide. Accordingly, an immobilized set of fragments from a given polypeptide can be separated from at least 1, 2, 3, 4, 5 or more fragments from the given polypeptide. The combined amino acid sequence content of fragments that are not linked to a particle can include less than 50%, 40%, 30%, 20%, 10%, 5% or less of the mass (or amino acid sequence content) of the polypeptide from which the fragments were obtained.

A method of the present disclosure can include a step of performing a binding assay including contacting a set of polypeptide fragments with one or more affinity reagents and detecting binding of the affinity reagent(s) to the set of polypeptide fragments. Individual polypeptide fragments of the set of fragments need not be spatially resolved by the detector used. As such, the set of fragments can be detected as an ensemble and at a resolution that is substantially the same as detecting the polypeptide from which the set of fragments is derived. In some configurations, the set of polypeptide fragments is attached to a particle as an immobilized set of polypeptide fragments while a binding assay is performed. Accordingly, set of polypeptide fragments that is attached to a particle can be contacted with one or more affinity reagents and binding of the affinity reagent(s) to the polypeptide fragments can be detected on the particle.

In some configurations of the present methods, a set of polypeptide fragments can be removed from a particle prior to being detected. The set of fragments can be manipulated and detected as an ensemble, whereby individual polypeptide fragments of the set of fragments are not spatially resolved from each other. For example, the set of fragments can be present in a fluid as a mixture and a binding assay can be carried out on the contents of the fluid. Optionally, a set of polypeptide fragments that is removed from a particle can be attached to another particle or to a solid support. For example, the set of polypeptide fragments can be attached to an address in an array and a binding assay can be carried out on the array.

If desired, one or more fragments in an immobilized set of polypeptide fragments on a particle can be removed from the particle and individually detected or manipulated. For example, the individual polypeptide fragments can be attached to respective particles or addresses in an array. The fragments can thus be individually resolved due to spatial separation of the particles or addresses in the array.

Any of a variety of affinity reagents can be used to detect polypeptides, whether the polypeptides are full length gene products, fragments thereof or various proteoforms. Affinity reagents and methods for their use will be exemplified herein in the context of detecting sets of polypeptide fragments. It will be understood that the examples can be extended to detection of full-length polypeptides or individual polypeptide fragments. Any molecule or other substance that is capable of specifically or reproducibly binding to a polypeptide can be used as an affinity reagent. An affinity reagent can be larger than, smaller than or the same size as the polypeptide to which it binds. An affinity reagent may form a reversible or irreversible bond with a polypeptide. An affinity reagent may bind with a polypeptide in a covalent or non-covalent manner. Affinity reagents may include reactive affinity reagents, catalytic affinity reagents (e.g., kinases, proteases, etc.) or non-reactive affinity reagents (e.g., antibodies or fragments thereof). An affinity reagent can be non-reactive and non-catalytic, thereby not permanently altering the chemical structure of a polypeptide to which it binds. Affinity reagents that can be particularly useful for binding to polypeptides include, but are not limited to, antibodies or functional fragments thereof (e.g., Fab' fragments, $F(ab')_2$ fragments, single-chain variable fragments (scFv), di-scFv, tri-scFv, or microantibodies), affibodies, affilins, affimers, affitins, alphabodies, anticalins, avimers, DARPins, monobodies, nanoCLAMPs, lectins or functional fragments thereof.

An affinity reagent can include a label. Exemplary labels include, without limitation, a fluorophore, luminophore, chromophore, nanoparticle (e.g., gold, silver, carbon nanotubes), heavy atom, radioactive isotope, mass label, charge label, spin label, receptor, ligand, nucleic acid barcode, polypeptide barcode, polysaccharide barcode, or the like. A label can produce any of a variety of detectable signals including, for example, an optical signal such as absorbance of radiation, luminescence (e.g. fluorescence or phosphorescence) emission, luminescence lifetime, luminescence polarization, or the like; Rayleigh and/or Mie scattering; magnetic properties; electrical properties; charge; mass; radioactivity or the like. A label may produce a signal with a characteristic frequency, intensity, polarity, duration, wavelength, sequence, or fingerprint. A label need not directly produce a signal. For example, a label can bind to a receptor or ligand having a moiety that produces a characteristic signal. Such labels can include, for example, nucleic acids that are encoded with a particular nucleotide sequence, avidin, biotin, non-peptide ligands of known receptors, or the like.

One or more affinity reagents used to detect a set of polypeptide fragments can recognize epitopes that lack particular amino acids. For example, one or more affinity reagents can recognize epitopes that lack amino acids of a type used to link polypeptide fragments to a particle. Accordingly, the epitopes can lack one or more of lysines, histidines, arginines, cysteines, methionines, aspartic acids, glutamic acids, serines, threonines, tyrosines, glutamines or asparagines. Alternatively, one or more affinity reagents can recognize amino acids having a linker moiety that is used to link polypeptide fragments to a particle. Accordingly, the epitopes can include one or more of a lysine analog, histidine analog, arginine analog, cysteine analog, methionine analog, aspartic acid analog, glutamic acid analog, serine analog, threonine analog, tyrosine analog, glutamine analog or asparagine analog, wherein the analog is the same or similar to the linker moiety used to link the polypeptide fragments to the particle. In some configurations of the methods set forth herein, one or more affinity reagents can recognize epitopes that lack amino acid sequences recognized by cleavage agents used to produce the polypeptide fragments. Accordingly, the epitopes can lack one or more of the sequences shown in Table 1, herein.

A set of polypeptide fragments can be detected in a fluid or on a solid support. For fluid configurations, a fluid containing a set of polypeptide fragments can be mixed with another fluid containing one or more affinity reagents. When on solid support, one or more sets of polypeptide fragments can be attached to a particle or solid support. Affinity reagents that will participate in a binding event can be contained in a fluid that is in contact with the particle or solid support.

Particle-attached sets of polypeptide fragments can be detected at single particle resolution. When the particle is attached to a set of fragments from a single polypeptide, resolution of one particle from another effectively achieves single polypeptide resolution. For example, single polypeptide resolution can be based on spatial or temporal separation of the set of fragments from sets of fragments derived from other polypeptides. For example, individual particle-attached sets of fragments can be located at different sites in an array. Alternatively to single-polypeptide resolution, a detection method can be carried out at ensemble-resolution or bulk-resolution. Bulk-resolution configurations acquire a composite signal from a plurality of different particles. A composite signal can be acquired from a population of multiple sets of polypeptide fragments, for example, in a well or cuvette, or on a solid support surface.

A set of polypeptide fragments can be contacted with a plurality of different affinity reagents. For example, a plurality of affinity reagents (whether configured separately or as a pool) may include at least 2, 5, 10, 25, 50, 100, 250, 500 or more types of affinity reagents, each type of affinity reagent differing from the other types with respect to the epitope(s) recognized. Alternatively or additionally, a plurality of affinity reagents may include at most 500, 250, 100, 50, 25, 10, 5, or 2 types of affinity reagents. Different types of affinity reagents in a pool can be uniquely labeled such that the different types can be distinguished from each other. In some configurations, at least two, and up to all, of the different types of affinity reagents in a pool may be indistinguishably labeled. Alternatively or additionally to the use of unique labels, different types of affinity reagents can be delivered and detected serially when evaluating polypeptides or sets of fragments from polypeptides.

Detection of multiple sets of polypeptide fragments can be performed in a multiplex format. In multiplexed formats, different sets of fragments can be attached to different unique identifiers (e.g. sites in an array), and the sets can be manipulated and detected in parallel. For example, a fluid containing one or more different affinity reagents can be delivered to an array of addresses, each address having an immobilized set of polypeptide fragments, such that the addresses of the array are in simultaneous contact with the affinity reagent(s). The sets of polypeptides can be attached to the respective addresses via particles or, alternatively, the sets of polypeptides can be directly attached to the respective addresses. Moreover, a plurality of addresses can be observed in parallel allowing for rapid detection of binding events. Multiple sets of polypeptide fragments can be derived from a proteome or subfraction of a proteome.

A set of polypeptide fragments can be attached to a unique identifier using any of a variety of means. The set of fragments can be attached to a particle and the particle can be attached to an address on a solid support or to another unique identifier. Exemplary attachments include, but are not limited to, covalent or non-covalent attachments set forth herein in the context of attaching polypeptides, or fragments thereof, to particles. Exemplary reagents and methods for attaching structured nucleic acid particles to solid supports are set forth in US Pat. App. Pub. No.

2021/0101930 A1 or U.S. Pat. No. 11,505,796 (U.S. patent application Ser. No. 17/692,035), each of which is incorporated herein by reference.

Binding can be detected using any of a variety of techniques that are appropriate to the assay components used. For example, binding can be detected by acquiring a signal from a label attached to an affinity reagent when bound to a set of polypeptide fragments, acquiring a signal from a label attached to set of polypeptide fragments when bound to an affinity reagent, or signal(s) from labels attached to an affinity reagent and polypeptide fragment to which the affinity reagent is bound (e.g. signals produced via Förster resonance transfer between a label on the affinity reagent and a label on a polypeptide fragment). In some configurations a complex between an affinity reagent and a polypeptide fragment need not be directly detected, for example, in formats where a nucleic acid tag or other moiety is created or modified as a result of binding. Optical detection techniques such as luminescent intensity detection, luminescence lifetime detection, luminescence polarization detection, or surface plasmon resonance detection can be useful. Other detection techniques include, but are not limited to, electronic detection such as techniques that utilize a field-effect transistor (FET), ion-sensitive FET, or chemically-sensitive FET. Exemplary methods are set forth in U.S. Pat. No. 10,473,654 or U.S. Pat. App. Pub. No. 2022/0162684 A1, each of which is incorporated herein by reference.

Optionally, a method set forth herein can be configured to detect interactions between an affinity reagent and a polypeptide fragment. In a first configuration, an affinity reagent can be attached to a first fluorophore, a polypeptide fragment can be attached to a second fluorophore and interactions between the affinity reagent and polypeptide fragment can be detected via Förster resonance energy transfer (FRET) between the first fluorophore and second fluorophore. Optionally, the second fluorophore can be attached to the polypeptide fragment by virtue of being attached to a linker that also attaches the polypeptide fragment to a particle. In some cases, the linker can include a nucleic acid having a first nucleotide sequence that is complementary to a second nucleotide sequence on a nucleic acid that is attached to the affinity reagent. Hybridization of the first and second nucleotide sequences can position the first and second fluorophore for FRET. In a second configuration, an affinity reagent can be attached to a first nucleic acid, a polypeptide fragment can be attached to a second nucleic acid having a sequence that is complementary to a sequence of the first nucleic acid and interactions between the affinity reagent and polypeptide fragment can be detected via hybridization of the complementary sequences. For example, hybridization can be detected by modifying one of the complementary nucleic acids in the presence of the other nucleic acid. The modification can be, for example, ligation to produce a detectable product (e.g. a labeled oligonucleotide can be ligated to one of the nucleic acids and then detected), or polymerase extension to produce a detectable product (e.g. one or more labeled nucleotide can be added to one of the nucleic acids and then detected).

In some configurations of the methods set forth herein, individual polypeptide fragments can be attached to a given particle via unique linkers. For example, each polypeptide fragment can be attached to a linker having a different nucleotide sequence. The nucleotide sequences can function as barcodes or tags that are uniquely associated with the fragments. As such, each fragment from a given polypeptide can be distinguished from other fragments from the polypeptide by virtue of the linker to which it is attached. Alternatively or additionally, the nucleotide sequences can identify the particle to which polypeptide fragments are attached. As such, each particle can include a plurality of linkers that share a common barcode sequence but each particle can be associated with a different barcode sequence. In this case, any polypeptide fragment that is attached to a nucleic acid having the common barcode sequence can be traced back to the polypeptide from which the polypeptide fragments were derived. In this example, polypeptide fragments and their attached linkers can be released from a plurality of particles and the different sequence of the linkers can be detected to determine which fragments were derived from a given polypeptide.

A set of polypeptide fragments can be detected by obtaining multiple separate and non-identical measurements of the set. In particular configurations, the individual measurements may not, by themselves, be sufficiently accurate or specific to make the characterization, but an aggregation of the multiple non-identical measurements can allow a characterization to be made with a high degree of accuracy, specificity and confidence. For example, the multiple separate measurements can include subjecting the set of polypeptide fragments to reagents that are promiscuous with regard to recognizing multiple different polypeptides suspected of being present in a given sample from which the set is derived. The use of promiscuous reagents can be particularly powerful in a multiplex format in which sets of polypeptide fragments from multiple different polypeptides are characterized in parallel. Accordingly, a first measurement carried out using a first promiscuous reagent may perceive a first subgroup of the different sets of fragments without differentiating the identity of one set in the subgroup from another set in the subgroup. A second measurement carried out using a second promiscuous reagent may perceive a second subgroup of fragment sets, again, without differentiating the identity of one fragment set in the second subgroup from another fragment set in the second subgroup. However, a comparison of the first and second measurements can distinguish: (i) a fragment set that is uniquely present in the first subgroup but not the second subgroup; (ii) a fragment set that is uniquely present in the second subgroup but not the first subgroup; (iii) a fragment set that is uniquely present in both the first and second subgroups; or (iv) a fragment set that is uniquely absent in the first and second subgroups. The number of promiscuous reagents used, the number of separate measurements acquired, and degree of reagent promiscuity (e.g. the diversity of fragment sets recognized by the reagent) can be adjusted to suit the polypeptide diversity expected for a particular sample from which the fragment sets are derived.

In particular configurations, a set of polypeptide fragments can be detected using one or more affinity reagents having known or measurable binding affinity for the polypeptide from which the set is derived. For example, an affinity reagent can bind a set of fragments to form a complex with at least one of the fragments and a signal produced by the complex can be detected. A set of polypeptide fragments that is detected by binding to a known affinity reagent can be identified based on the known or predicted binding characteristics of the affinity reagent. For example, an affinity reagent that is known to selectively recognize a candidate polypeptide suspected of being in a sample, without substantially binding to other polypeptides in the sample, can be used to identify an instant polypeptide in the sample as being the candidate polypeptide merely by observing binding of the affinity reagent to a set of fragments derived from the instant polypeptide. This one-to-one correlation of affinity reagent to candidate polypeptide can be used for identification of one or more polypeptides. However, as the polypeptide complexity (i.e. the number and variety of different polypeptides) in a sample increases, or as the number of different candidate polypeptides to be identified increases, the time and resources to produce a commensurate variety of affinity reagents having one-to-one specificity for fragment sets derived from the polypeptides approaches limits of practicality.

Methods set forth herein, can be advantageously employed to overcome these constraints. In particular configurations, the methods can be used to identify a number of different candidate polypeptides that exceeds the number of affinity reagents used. For example, the number of candidate polypeptides identified can be at least 5 fold, 10 fold, 25 fold, 50 fold, 100 fold or more than the number of affinity reagents used. This can be achieved, for example, by (1) using promiscuous affinity reagents that recognize multiple different candidate polypeptides suspected of being present in a given sample, and (2) subjecting sets of polypeptide fragments from the sample to a set of promiscuous affinity reagents that, taken as a whole, are expected to bind the set of fragments from each polypeptide in a different combination, such that each polypeptide is expected to produce a unique profile of binding and non-binding events. Promiscuity of an affinity reagent is a characteristic that can be understood relative to a given population of polypeptides. Promiscuity can arise due to the affinity reagent recognizing an epitope that is known to be present in a plurality of different candidate polypeptides, wherein the candidate polypeptides are suspected of being present in the given population of polypeptides. For example, epitopes having relatively short amino acid lengths such as dimers, trimers, or tetramers are expected to occur in a substantial number of different polypeptides in the human proteome. Alternatively or additionally, a promiscuous affinity reagent can recognize different epitopes (i.e. epitopes having a variety of different structures), the different epitopes being present in a plurality of different candidate polypeptides. For example, a promiscuous affinity reagent that is designed or selected for its affinity toward a first trimer epitope may bind to a second epitope that has a different sequence of amino acids when compared to the first epitope.

Although performing a single binding reaction between a promiscuous affinity reagent and sets of polypeptide fragments derived from a complex sample of polypeptides may yield ambiguous results regarding the identity of the different polypeptides to which it binds, the ambiguity can be resolved when the results are combined with other identifying information about those polypeptides. The identifying information can include characteristics of the polypeptide such as length (i.e. number of amino acids), hydrophobicity, charge to mass ratio, isoelectric point, chromatographic fractionation behavior, enzymatic activity, presence or absence of post translational modifications or the like. The identifying information can include results of binding with other promiscuous affinity reagents. For example, a plurality of different promiscuous affinity reagents can be contacted with sets of polypeptide fragments derived from a complex sample of polypeptides, wherein the plurality is configured to produce a different binding profile for each candidate polypeptide suspected of being present in the population. In this example, each of the affinity reagents is distinguishable from the other affinity reagents, for example, due to unique labeling (e.g. different affinity reagents have different luminophore labels), unique spatial location (e.g. different affinity reagents are located at different sites in an array), and/or unique time of use (e.g. different affinity reagents are delivered in series to a population of polypeptides). Accordingly, the plurality of promiscuous affinity reagents produces a binding profile for each set of polypeptide fragments that can be decoded to identify a unique combination of epitopes present in the individual set, and this can in turn be used to identify the individual polypeptide from which the set is derived as a particular candidate polypeptide having the same or similar unique combination of epitopes. The binding profile can include observed binding events as well as observed non-binding events and this information can be compared to the presence and absence of epitopes, respectively, in a given candidate polypeptide to make a positive identification.

In some configurations, distinct and reproducible binding profiles may be observed for some or even a substantial majority of sets of polypeptide fragments that are to be identified in a sample. However, in many cases one or more binding events produces inconclusive or even aberrant results. For example, observation of binding outcome for a single-molecule binding event can be particularly prone to ambiguities due to stochasticity in the behavior of single molecules when observed using certain detection hardware. The present disclosure provides methods that provide accurate polypeptide identification despite ambiguities and imperfections that can arise in many contexts. In some configurations, methods for identifying, quantitating or otherwise characterizing one or more polypeptides in a sample utilize a binding model that evaluates the likelihood or probability that sets of polypeptide fragments from one or more candidate polypeptides will have produced an empirically observed binding profile. The binding model can include information regarding expected binding outcomes (e.g. binding or non-binding) for binding of one or more affinity reagent with sets of polypeptide fragments from one or more candidate polypeptides. The information can include a priori characteristics of a set of polypeptide fragments that is expected to be produced from a candidate polypeptide under particular conditions. For example, the total amino acid composition and amino acid sequence of the set of fragments derived from a given candidate polypeptide can be predicted based on the amino acid sequence of the candidate polypeptide, the number and location of cleavage sites in the candidate polypeptide, and the number and location of particle-linked amino acids in the candidate polypeptide. The composition of the set of fragments can differ due to changes in the cleavage site or type of amino acids linked to the particle. As such, the binding model can be created using cleavage site(s) and amino acid linkage sites that are consistent with those used in producing the observed sets of polypeptide fragments. Moreover, a binding model can include information regarding the propensity or likelihood of a given candidate polypeptide, or set of fragments derived therefrom, generating a false positive or false negative binding result in the presence of a particular affinity reagent.

Methods set forth herein can be used to evaluate the degree of compatibility of one or more empirical binding profiles (e.g. obtained from one or more sets of polypeptide fragments) with results computed for various candidate polypeptides using a binding model. For example, to identify an unknown polypeptide in a sample of many polypeptides, an empirical binding profile for a set of fragments derived from the polypeptide can be compared to results computed by the binding model for sets of fragments derived from many or all candidate polypeptides suspected of being in the sample. In some configurations of the methods set forth herein, identity for the unknown polypeptide is determined based on a likelihood of the set of fragments derived from the unknown polypeptide being a set of fragments derived from a particular candidate polypeptide given the empirical binding pattern, or based on the probability of a set of fragments from the particular candidate polypeptide generating the empirical binding pattern. Optionally a score can be determined from the measurements that are acquired for the set of fragments derived from the unknown polypeptide with respect to sets of fragments from many or all candidate polypeptides suspected of being in the sample. A digital or binary score that indicates one of two discrete states can be determined. In particular configurations, the score can be non-digital or non-binary. For example, the score can be a value selected from a continuum of values such that an identity is made based on the score being above or below a threshold value. Moreover, a score can be a single value or a collection of values. Particularly useful methods for identifying polypeptides using promiscuous reagents, serial binding measurements and/or decoding with binding models are set forth, for example, in U.S. Pat. No. 10,473,654 US Pat. App. Pub. No. 2020/0318101 A1 or Egertson et al., *BioRxiv* (2021), DOI: 10.1101/2021.10.11.463967, each of which is incorporated herein by reference.

A method of the present disclosure can include a step of identifying a polypeptide from results of a binding assay. The identification can include determining the amino acid sequence of the polypeptide, for example, based on the combination of epitopes detected in a set of fragments from the polypeptide. The amino acid sequences for a plurality of candidate polypeptides can be evaluated for the presence of the combination of detected epitopes. Optionally, the amino acid sequences for the plurality of candidate polypeptides can also be evaluated for absence of epitopes that were determined not to be present in the set of fragments. For example, one or more epitopes may be present in a fragment of a polypeptide that lacks amino acids that are capable of attaching to the particle when cleaved from the full length polypeptide. As such, the fragment is expected to be absent from the particle following cleavage of the polypeptide. A polypeptide can be identified based on a prediction of the epitopes that are expected to be present in a set of polypeptide fragments derived from the polypeptide. The prediction can be based on the known number and location of cleavage sites in the polypeptide for the cleavage agent used to produce the set of fragments and can be further based on the known number and location of amino acids in the polypeptide that are expected to be linked to the particle as a product of the linking chemistry used. Identification can also be determined based on evaluation of the consistency between empirical binding patterns and binding models, for example, as set forth above.

Optionally, each candidate polypeptide that is used to decode assay results can be represented as a subset of sequence fragments that is expected to be attached to a given particle using a particular combination of cleavage reagents and polypeptide attachment chemistries used for the assay. At least some of the candidate polypeptides would likely have a net reduction in amino acid sequence content due to loss of the fragments that are not expected to be retained on a particle following use of a particular combination of cleavage agents and polypeptide attachment chemistries. Accordingly, decoding methods set forth in U.S. Pat. No. 10,473,654, US Pat. App. Pub. No. 2020/0318101 A1 or Egertson et al., *BioRxiv* (2021), DOI: 10.1101/2021.10.11.463967 can be modified to replace full length candidate polypeptide sequences with subsets of sequences expected to result from a particular combination of cleavage agents and polypeptide attachment chemistries used for the assay that is to be decoded.

Identification of a polypeptide can include determining the presence of one or more post-translational modifications in a polypeptide, determining the location of one or more post-translational modifications in the sequence of the polypeptide, or determining the number of post-translational modifications in the polypeptide. A polypeptide can also be identified based on detection of particular characteristics such as polypeptide length, pKa, charge, mass, or enzymatic activity.

Optionally, a method of the present disclosure can be configured to include performance of a binding assay on a polypeptide and performance of a binding assay on a set of fragments derived from the polypeptide. The results of the two assays can be evaluated in view of each other to identify or characterize the polypeptide. For example, one or more epitopes may be more accessible to affinity reagents in the set of fragments than in the non-fragmented polypeptide. Conversely, one or more epitopes that are detected in the non-fragmented polypeptide may not be present in any fragments that are retained in the fragment set. In such situations, a combination of results from assays of both the fragment set and the non-fragmented polypeptide may provide a more accurate identification of the polypeptide.

Accordingly, a method of identifying a polypeptide can include steps of (a) attaching a polypeptide to a particle, thereby producing an immobilized polypeptide having a plurality of amino acids linked to the particle; (b) performing a binding assay including contacting the immobilized polypeptide with a plurality of affinity reagents and detecting binding of affinity reagents of the plurality of affinity reagents to the polypeptide; (c) fragmenting the immobilized polypeptide, whereby the particle is attached to a set of fragments of the polypeptide; (d) performing a second binding assay including contacting the set of fragments with a plurality of affinity reagents and detecting binding of affinity reagents of the plurality of affinity reagents to the set of fragments; and (e) identifying the polypeptide from results of the binding assay and second binding assay. Binding assays can be carried out using immobilized polypeptides in place of immobilized sets of polypeptide fragments in binding assays set forth herein.

Optionally, the immobilized polypeptide can be in a denatured conformation during a binding assay or other detection technique set forth herein. Any of a variety of denaturants can be used such as heat (e.g. temperatures greater than about 40 °C, 60 °C, 80 °C or higher), excessive pH (e.g. pH lower than 4.0, 3.0 or 2.0; or pH greater than 10.0, 11.0 or 12.0); chaotropic agents (e.g. urea, guanidinium chloride, or sodium dodecyl sulfate), organic solvent (e.g. chloroform or ethanol), physical agitation (e.g. sonication) or radiation. Alternatively, the immobilized polypeptide can be in a native conformation during the binding assay. Generally, a polypeptide will retain biological activity when in a native conformation.

Optionally, a method of the present disclosure can be configured to perform a first assay on a first set of polypeptide fragments and to perform a second assay on a second set of polypeptide fragments. The method can include steps for attaching polypeptides to particles and for fragmenting the attached polypeptides to produce the respective first and second immobilized sets of polypeptide fragments. Although the same type of polypeptide may be used to produce the respective immobilized sets of fragments (e.g.

the polypeptides can be obtained from aliquots of a common sample), the conditions for the attachment step and/or the fragmentation step can differ. As such, the first immobilized set of polypeptide fragments can differ from the second immobilized set of polypeptide fragments. Differences in the results of binding assays performed on the respective fragment sets can provide useful information regarding the identity or structural characteristics of the protein from which the two sets of fragments are derived.

Accordingly, a method of identifying or characterizing a polypeptide can include steps of (a) attaching a first polypeptide to a particle, wherein the first polypeptide is from a biological sample, thereby producing a first immobilized polypeptide having a plurality of amino acids linked to the particle; (b) fragmenting the first immobilized polypeptide, whereby the particle is attached to a first set of fragments; (c) performing a binding assay including contacting the first set of fragments with a plurality of affinity reagents and detecting binding of affinity reagents of the plurality of affinity reagents to the first set of fragments; (d) attaching a second polypeptide to a second particle, wherein the second polypeptide is from the biological sample, thereby producing a second immobilized polypeptide comprising a plurality of amino acids linked to the particle; (e) fragmenting the second immobilized polypeptide, whereby the second particle is attached to a second set of fragments of the second polypeptide; and (f) performing a binding assay including contacting the second set of fragments with the plurality of affinity reagents and detecting binding of the affinity reagents of the plurality of affinity reagents to fragments of the second set of fragments.

In particular configurations of the above method, the first polypeptide can have an amino acid sequence that is substantially identical to an amino acid sequence of the second polypeptide. For example, the complete amino acid sequence of the first polypeptide can be identical to the complete amino acid sequence of the second polypeptide. In some cases, a substantial portion of the amino acid sequence for the first polypeptide can be identical to a substantial portion of the amino acid sequence for the second polypeptide. For example, at least about 75%, 80%, 90%, 95%, 99% or more of the amino acid sequence of the first polypeptide can be identical to an amino acid sequence for the second polypeptide.

The first and second polypeptides can be obtained from aliquots partitioned from a single sample. The sample can contain multiple copies of a single polypeptide sequence, for example, multiple copies produced from the same gene. For example, the sample can contain a purified polypeptide sample. Alternatively, the sample can contain multiple copies of a plurality of different polypeptide sequences, for example, multiple copies produced from multiple genes. As such, the sample can contain a proteome or substantial fraction of a proteome.

The first and second polypeptides can be contained in separate vessels for some or all steps of the above method. Similarly, the first and second sets of polypeptide fragments can be contained in separate vessels for some or all of the steps. For example, steps (a) and (d) can occur in separate vessels; steps (b) and (e) can occur in separate vessels; and/or steps (c) and (f) can occur in separate vessels. If desired, the first and second polypeptides can be contained in the same vessel for some or all steps of the above method. For example, steps (a) and (d) can occur simultaneously in the same vessel; steps (b) and (e) can occur simultaneously in the same vessel; and/or steps (c) and (f) can occur simultaneously in the same vessel. Optionally, the first and second polypeptides can be contained in separate vessels for at least one step and then merged into a common vessel for at least one other step. For example, steps (a) and (b) can occur in a first vessel; steps (d) and (e) can occur in a second vessel; and steps (c) and (f) can occur in the same vessel. For configurations wherein the first and second polypeptides are contained in the same vessel, the polypeptides can be tagged, for example with unique identifiers to allow them to be distinguished. Similarly, tags can be used to distinguish the first and second sets of polypeptide fragments that are contained in the same vessel. Particularly useful tags include nucleic acid tags which can be readily attached to particles such as structured nucleic acid particles to which polypeptides or sets of fragments are attached.

In a first configuration of the above method, the first immobilized polypeptide can be linked to the particle via amino acid types that are different from amino acid types that link the second immobilized polypeptide to the second particle. In this first configuration, the first immobilized polypeptide can be fragmented with a first protease and the second immobilized polypeptide can be fragmented by a second protease, the first protease recognizing a different cleavage site than the cleavage site recognized by the second protease. The combination of differing linkages and differing sites of cleavage can produce different sets of polypeptide fragments even if the first polypeptide has the same amino acid sequence as the second polypeptide.

In a second configuration of the above method, the first immobilized polypeptide can be linked to the particle via amino acid types that are different from amino acid types that link the second immobilized polypeptide to the second particle. In this second configuration, the first immobilized polypeptide and the second immobilized polypeptide can be fragmented by the same proteases or by proteases recognizing the same cleavage site. The use of differing linkages can produce different sets of polypeptide fragments even if the first polypeptide has the same amino acid sequence as the second polypeptide and the polypeptides are cleaved using the same proteases.

In a third configuration of the above method, the first immobilized polypeptide can be linked to the particle via amino acid types that are the same as the amino acid types that link the second immobilized polypeptide to the second particle. In this third configuration, the first immobilized polypeptide can be fragmented with a first protease and the second immobilized polypeptide can be fragmented by a second protease, the first protease recognizing a different cleavage site than the cleavage site recognized by the second protease. The use of differing sites of cleavage can produce different sets of polypeptide fragments even if the first polypeptide has the same amino acid sequence as the second polypeptide and the polypeptides are linked to particles via the same types of amino acids.

In a fourth configuration of the above method, the first immobilized polypeptide can be linked to the particle via amino acid types that are the same as the amino acid types that link the second immobilized polypeptide to the second particle. In this fourth configuration, the first immobilized polypeptide and the second immobilized polypeptide can be fragmented by the same proteases or by proteases recognizing the same cleavage site. The fourth configuration would be expected to produce substantially similar sets of polypeptide fragments. As such, the first polypeptide can be processed as a control for the second polypeptide.

The methods set forth herein are particularly useful for multiplex assays wherein a large number and variety of polypeptides are manipulated and detected in parallel. For example, a method of the present disclosure can be configured to capture polypeptides individually, cleave each polypeptide to produce a captured set of polypeptide fragments, contact a plurality of the captured sets with one or more affinity reagents, and detect binding of the affinity reagent(s) to the plurality of captured sets. The binding and detection steps can be conducted in parallel, for example, by delivering affinity reagents to an array of the captured sets of polypeptide fragments and by detecting the array in parallel.

Accordingly, the present disclosure provides a method of identifying polypeptides, including steps of (a) attaching a plurality of polypeptides to a plurality of particles, thereby producing a plurality of immobilized polypeptides, each of the immobilized polypeptides having a plurality of amino acids linked to a particle of the plurality of particles; (b) fragmenting the plurality of immobilized polypeptides, thereby producing a plurality of immobilized fragment sets, wherein the immobilized fragment sets remain attached to the particles via the linked amino acids; (c) performing a binding assay including contacting the plurality of immobilized fragment sets with a plurality of affinity reagents and detecting binding of the plurality of affinity reagents to the plurality of immobilized fragment sets; and (d) identifying polypeptides of the plurality of polypeptides from results of the binding assay.

The content of a plurality of polypeptides can be understood according to any of a variety of characteristics such as those set forth below or elsewhere herein. These characteristics can apply to a sample of polypeptides present at one or more steps of a method set forth herein. The characteristics can apply, for example, to a plurality of fluid-phase polypeptides or a plurality of immobilized polypeptides.

A plurality of polypeptides can be characterized in terms of total polypeptide mass. The total mass of polypeptide in a liter of plasma has been estimated to be 70 g and the total mass of polypeptide in a human cell has been estimated to be between 100 pg and 500 pg depending upon cells type. See Wisniewski et al. *Molecular & Cellular Proteomics* 13:10.1074/mcp.M113.037309, 3497-3506 (2014), which is incorporated herein by reference. A plurality of polypeptides can include at least 1 pg, 10 pg, 100 pg, 1 ng, 10 ng, 100 ng, 1 mg, 10 mg, 100 mg, 1 mg, 10 mg, 100 mg or more polypeptide by mass. Alternatively or additionally, a plurality of polypeptides may contain at most 100 mg, 10 mg, 1 mg, 100 mg, 10 mg, 1 mg, 100 ng, 10 ng, 1 ng, 100 pg, 10 pg, 1 pg or less polypeptide by mass.

A plurality of polypeptides can include or be obtained from a proteomic sample. A proteomic sample can include substantially all polypeptides from a given source or a substantial fraction thereof. For example, a proteomic sample may contain at least 60%, 75%, 90%, 95%, 99%, 99.9% or more of the total polypeptide mass present in the source from which the sample was derived. Alternatively or additionally, a proteomic sample may contain at most 99.9%, 99%, 95%, 90%, 75%, 60% or less of the total polypeptide mass present in the source from which the sample was derived.

A plurality of polypeptides can be characterized in terms of total number of polypeptide molecules. The total number of polypeptide molecules in a *Saccharomyces cerevisiae* cell has been estimated to be about 42 million polypeptide molecules. See Ho et al., *Cell Systems* (2018), DOI: 10.1016/j.cels.2017.12.004, which is incorporated herein by reference. A plurality of polypeptides used or included in a method, composition or apparatus set forth herein can include at least 1 polypeptide molecule, 10 polypeptide molecules, 100 polypeptide molecules, $1\times10^4$ polypeptide molecules, $1\times10^6$ polypeptide molecules, $1\times10^8$ polypeptide molecules, $1\times10^{10}$ polypeptide molecules, 1 mole ($6.02214076\times10^{23}$ molecules) of polypeptide molecules, 10 moles of polypeptide molecules, 100 moles of polypeptide molecules or more. Alternatively or additionally, a plurality of polypeptides may contain at most 100 moles of polypeptide molecules, 10 moles of polypeptide molecules, 1 mole of polypeptide molecules, $1\times10^{10}$ polypeptide molecules, $1\times10^8$ polypeptide molecules, $1\times10^6$ polypeptide molecules, $1\times10^4$ polypeptide molecules, 100 polypeptide molecules, 10 polypeptide molecules, 1 polypeptide molecule or less.

A plurality of polypeptides can be characterized in terms of the variety of full-length amino acid sequences in the plurality. For example, the variety of full-length amino acid sequences in a plurality of polypeptides can be equated with the number of different polypeptide-encoding genes in the source for the plurality of polypeptides. Whether or not the polypeptides are derived from a known genome or from any genome at all, the variety of full-length amino acid sequences can be counted independent of presence or absence of post translational modifications in the polypeptides. A human proteome is estimated to have about 20,000 different polypeptide-encoding genes such that a plurality of polypeptides derived from a human can include up to about 20,000 different full-length amino acid sequences. See Aebersold et al., *Nat. Chem. Biol.* 14:206-214 (2018), which is incorporated herein by reference. Other genomes and proteomes in nature are known to be larger or smaller. A plurality of polypeptides used or included in a method, composition or apparatus set forth herein can have a complexity that includes substantially all different native-length amino acid sequences from a given source. A proteome or subfraction can have a complexity of at least 2, 5, 10, 100, $1\times10^3$, $1\times10^4$, $2\times10^4$, $3\times10^4$ or more different native-length amino acid sequences. Alternatively or additionally, a proteome or subfraction can have a complexity that is at most $3\times10^4$, $2\times10^4$, $1\times10^4$, $1\times10^3$, 100, 10, 5, 2 or fewer different native-length amino acid sequences.

The diversity of a proteomic sample can include at least one representative for substantially all polypeptides encoded by a source from which the sample was derived or a substantial fraction thereof. For example, a proteomic sample may contain at least one representative for at least 60%, 75%, 90%, 95%, 99%, 99.9% or more of the polypeptides encoded by a source from which the sample was derived. Alternatively or additionally, a proteomic sample may contain a representative for at most 99.9%, 99%, 95%, 90%, 75%, 60% or less of the polypeptides encoded by a source from which the sample was derived.

A plurality of polypeptides can be characterized in terms of the variety of full-length amino acid sequences in the plurality including transcribed splice variants. The human proteome has been estimated to include about 70,000 different full-length amino acid sequences when splice variants ae included. See Aebersold et al., *Nat. Chem. Biol.* 14:206-214 (2018), which is incorporated herein by reference. A plurality of polypeptides used or included in a method, composition or apparatus set forth herein can have a complexity of at least 2, 5, 10, 100, $1\times10^3$, $1\times10^4$, $7\times10^4$, $1\times10^5$, $1\times10^6$ or more different full-length amino acid sequences. Alternatively or additionally, a plurality of polypeptides can have a complexity that is at most $1\times10^6$, $1\times10^5$, $7\times10^4$, $1\times10^4$, $1\times10^3$, 100, 10, 5, 2 or fewer different full-length amino acid sequences.

A plurality of polypeptides can be characterized in terms of the variety of polypeptide structures in the plurality including different full-length amino acid sequences and different proteoforms among those sequences. Different molecular forms of polypeptides expressed from a given gene are considered to be different proteoforms. Proteoforms can differ, for example, due to differences in primary structure (e.g. shorter or longer amino acid sequences), different arrangement of domains (e.g. transcriptional splice variants), or different post translational modifications (e.g. presence or absence of phosphoryl, glycosyl, acetyl, or ubiquitin moieties). The human proteome is estimated to include hundreds of thousands of polypeptides when counting the different primary structures and proteoforms. See Aebersold et al., *Nat. Chem. Biol.* 14:206-214 (2018), which is incorporated herein by reference. A plurality of polypeptides used or included in a method, composition or apparatus set forth herein can have a complexity of at least 2, 5, 10, 100, $1\times10^3$, $1\times10^4$, $1\times10^5$, $1\times10^6$, $5\times10^6$, $1\times10^7$ or more different polypeptide structures. Alternatively or additionally, a plurality of polypeptides can have a complexity that is at most $1\times10^7$, $5\times10^6$, $1\times10^6$, $1\times10^5$, $1\times10^4$, $1\times10^3$, 100, 10, 5, 2 or fewer different polypeptide structures.

A plurality of polypeptides can be characterized in terms of the dynamic range for the different polypeptide structures in the sample. The dynamic range can be a measure of the range of abundance for all different polypeptide structures in a plurality of polypeptides, the range of abundance for all different primary polypeptide structures in a plurality of polypeptides, the range of abundance for all different full-length primary polypeptide structures in a plurality of polypeptides, the range of abundance for all different full-length gene products in a plurality of polypeptides, the range of abundance for all different proteoforms expressed from a given gene, or the range of abundance for any other set of different polypeptides set forth herein. The dynamic range for all polypeptides in human plasma is estimated to span more than 10 orders of magnitude from albumin, the most abundant polypeptide, to the rarest polypeptides that have been measured clinically. See Anderson and Anderson *Mol Cell Proteomics* 1:845-67 (2002), which is incorporated herein by reference. The dynamic range for plurality of polypeptides set forth herein can be a factor of at least 10, 100, $1\times10^3$, $1\times10^4$, $1\times10^6$, $1\times10^8$, $1\times10^{10}$, or more. Alternatively or additionally, the dynamic range for plurality of polypeptides set forth herein can be a factor of at most $1\times10^{10}$, $1\times10^8$, $1\times10^6$, $1\times10^4$, $1\times10^3$, 100, 10 or less.

A sample used herein need not be from a biological source and can instead be from a synthetic source, such as a library from a combinatorial synthesis or a library from an in vitro synthesis that exploits biological components. A synthetic sample can have a range of complexity similar to those set forth herein for proteomes. A method set forth herein can detect, identify or characterize some or all polypeptides in a proteome or other sample including, for example, at least about 1%, 5%, 10%, 25%, 50%, 75%, 90% or 99% of the polypeptides in the sample.

A multiplex configuration of a method set forth herein can include a step of attaching a plurality of polypeptides to a plurality of particles, thereby producing a plurality of immobilized polypeptides, each of the immobilized polypeptides having a plurality of amino acids linked to a particle of the plurality of particles. In a multiplex configuration, a pool of particles can be contacted with a pool of polypeptides such that a given particle can contact multiple polypeptides in the pool during the course of the attachment reaction and a given polypeptide can contact multiple particles in the pool during the course of the attachment reaction. As set forth in the context of FIGS. 2 through 6, the type of attachment chemistry used and the timing of performing various steps of the attachment process can be tailored to produce populations of immobilized polypeptides in which only a single polypeptide is attached to each particle.

In particular configurations of a method or composition set forth herein, individual immobilized polypeptides of a plurality of immobilized polypeptides can each include a single particle of the plurality of particles attached to a single polypeptide of the plurality of polypeptides. Alternatively or additionally, individual particles of the plurality of immobilized polypeptides can each include a single polypeptide of the plurality of polypeptides attached to the particle.

Particles can be contacted with polypeptides in a slurry. A slurry can provide the advantage of relatively high rates of contact between fluid-phase polypeptides and particles to which they will attach, while maintaining separability of attached polypeptides from each other. In some configurations of the methods set forth herein, particles can be attached to a solid support, for example, each particle can be attached to an address in an array of particles. Particles can be immobilized in this way prior to or during a step of attaching polypeptides to the particles. This format can be advantageous to maintain separation of immobilized polypeptides throughout the attachment process. This format can further be used to inhibit multiple particles from attaching to a single polypeptide.

The use of particles in the methods and compositions of the present disclosure is exemplary. Particles can be replaced by addresses on an array or other platforms that allow the polypeptides and sets of polypeptide fragments to be maintained as separate from each other. In an alternative configuration, individual particles of a plurality of particles can be partitioned into vessels and individual polypeptides of a plurality of polypeptides can be partitioned into the vessels during an attachment step set forth herein. The vessels can be tubes, wells or other containers that are appropriate for laboratory use. Other vessels include droplets or vesicles such as those that can be created or manipulated in an emulsion, fluid stream or droplet actuator. Individual particles can be present in each vessel such that individual vessels each contain a single polypeptide and a single particle. As such, the attachment reaction can yield individual particles attached to a single polypeptide. Emulsions including droplets can be formed to include particles and other reactants using techniques known in the art such as those set forth in U.S. Pat. App. Publ. Nos. 2005/0042648 A1; 2005/0079510 A1 and 2005/0130173 A1, and WO 05/010145, each of which is incorporated herein by reference. For examples of droplet actuators, see U.S. Pat. Nos. 6,911,132; 6,773,566; 6,565,727; 7,547,380; 7,641,779; 6,977,033; or 7,052,244, each of which is incorporated herein by reference.

A multiplex configuration of a method set forth herein can include a step of fragmenting a plurality of immobilized polypeptides, thereby producing an immobilized set of polypeptide fragment. The immobilized fragment sets can optionally remain attached to the particles via linkages to amino acids of the fragments. In a multiplex configuration, a plurality of immobilized polypeptides can be in simultaneous contact with a fluid containing cleaving agents, such as proteases. As such, a given cleaving agent can be in diffusional contact with multiple immobilized polypeptides. For example, a single protease can cleave multiple polypeptides in the reaction. Alternatively, a plurality of polypeptides can be individually and discretely contacted with a cleaving agent, for example, in separate vessels.

In particular configurations of a method or composition set forth herein, individual immobilized sets of fragments, each derived from a single polypeptide, can each include a single particle. Alternatively or additionally, individual particles can each be attached to a set of fragments from a single polypeptide.

Immobilized polypeptides can be contacted with cleaving agents in a slurry. In some configurations of the methods set forth herein, immobilized polypeptides can be attached to addresses on a support, for example, as an array of immobilized polypeptides, prior to or during the step of cleaving the polypeptides to form immobilized sets of polypeptide fragments. The use of particles in this step is exemplary. Particles can be replaced by addresses on an array or other platforms that allow the polypeptides and sets of polypeptide fragments to be maintained as separate from each other. For example, individual immobilized polypeptides of a plurality of immobilized polypeptides can be partitioned into vessels in the presence of cleaving agents and the immobilized sets of fragments that are produced can be partitioned into the vessels. The vessels can be those set forth above in the context of partitioning particles and polypeptides.

A multiplex configuration of a method set forth herein can include a step of performing a binding assay including contacting a plurality of sets of polypeptide fragments with a plurality of affinity reagents and detecting binding of the plurality of affinity reagents to the plurality of sets of polypeptide fragments. The individual sets of polypeptide fragments can be resolved from each other during the binding assay. For example, each set of polypeptide fragments can be attached to a particle as an immobilized set of polypeptide fragments while a binding assay is performed. Accordingly, a binding assay can be performed by contacting a plurality of immobilized sets of polypeptide fragments with a plurality of affinity reagents and detecting binding of the plurality of affinity reagents to the plurality of immobilized sets of polypeptide fragments. Optionally, individual immobilized fragment sets of a plurality of immobilized fragment sets can be spatially resolved from each other by the detection technique used. However, individual polypeptide fragments within any individual set of fragments need not be spatially resolved from each other when detected in various configurations of the methods set forth herein. As such, each immobilized set of polypeptide fragments can be detected as an ensemble and at a resolution that is substantially the same as detecting the individual polypeptide from which the set of fragments is derived.

A plurality of immobilized sets of polypeptide fragments can be contacted with affinity reagents in a slurry. Binding can be detected in a fluid array format or on a solid support. Exemplary fluid arrays include, but are not limited to, detection of particles in a fluid stream such as occurs in a fluorescence activated cell sorting apparatus. Turning to the example of a configuration using a solid support, binding can be detected in an array format, wherein individual particles are each attached to an address on the solid support. In some configurations of the methods set forth herein, immobilized sets of polypeptide fragments can be attached to addresses on a solid support when contacted with affinity reagents. For example, the sets of polypeptide fragments can each be attached to a particle and each particle can be attached to an address on the array when contacted with affinity reagents. Alternatively, contact with affinity reagents can occur when individual sets of polypeptide fragments are each be directly attached to an address of an array absent an intermediary particle.

In a multiplex configuration, a plurality of immobilized sets of polypeptide fragments can be in simultaneous contact with a fluid containing affinity reagents. As such, a given affinity reagent can be in diffusional contact with multiple immobilized sets of fragments. Alternatively, a plurality of immobilized sets of polypeptide fragments can be individually and discretely contacted with affinity reagents, for example, in separate vessels. For example, individual immobilized sets of polypeptide fragments can be partitioned into vessels in the presence of affinity reagents and binding can be detected in the vessels. The vessels can be those set forth above in the context of partitioning particles and polypeptides.

What is claimed is:

1. A method, comprising:

(a) attaching a polypeptide to a nucleic acid particle, wherein the polypeptide includes a plurality of first attachment moieties, wherein the nucleic acid particle includes a first linker composed of double stranded nucleic acid and having a single second attachment moiety reactive with one of the plurality of the first attachment moieties of the polypeptide thereby immobilizing the polypeptide to the nucleic acid particle;

(b) after attaching the polypeptide to the nucleic acid particle, modifying the nucleic acid particle by forming a plurality of second linkers on the nucleic acid particle, each of the second linkers having a first portion having double stranded nucleic acid and each of the second linkers having a single second attachment moiety reactive with one of the plurality of first attachment moieties of the polypeptide; and (c) fragmenting the immobilized polypeptide, thereby creating a set of polypeptide fragments that are individually immobilized to the nucleic acid particle via the first linker or the second linkers.

2. The method of claim 1, wherein the set of polypeptide fragments includes a first fragment attached to the nucleic acid particle via the first linker, and two or more fragments attached to the nucleic acid particle via the second linkers.

3. The method of claim 1, further comprising:

(d) performing a binding assay comprising contacting the set of polypeptide fragments with a plurality of affinity reagents and detecting binding of affinity reagents of the plurality of affinity reagents to the set of polypeptide fragments.

4. The method of claim 3, further comprising:

(e) characterizing the polypeptide from results of the binding assay.

5. The method of claim 4, wherein characterizing includes identifying the polypeptide from the results of the binding assay.

6. The method of claim 4, wherein characterizing includes quantifying the polypeptide in a sample.

7. The method of claim 1, wherein the polypeptide is a full-length polypeptide.

8. The method of claim 1, wherein the polypeptide immobilized to the nucleic acid particle is the only polypeptide immobilized to the nucleic acid particle.

9. The method of claim 1, wherein the plurality of second linkers each further have a second portion having single stranded nucleic acid.

10. The method of claim 1, wherein each of the plurality of second linkers are attached to the nucleic acid particle at predefined sites.

11. The method of claim 10, wherein the predefined sites correspond to single stranded nucleic acid regions of the nucleic acid particle.

12. The method of claim 1, further comprising:
(d) after attaching the polypeptide to the nucleic acid particle in step (b), modifying lengths of the plurality of second linkers.

13. The method of claim 12, wherein modifying lengths of the plurality of second linkers is shortening the lengths of the plurality of second linkers.

14. The method of claim 13, wherein the plurality of second linkers each include: (i) a first portion having the double stranded nucleic acid, and (ii) a second portion having single stranded nucleic acid, and shortening the lengths of the plurality of second linkers includes hybridizing complementary nucleic acid strands to the second portions having the single stranded nucleic acid.

15. The method of claim 1, wherein the first linker comprises a different nucleic acid sequence than the plurality of second linkers.

16. The method of claim 15, wherein the plurality of second linkers comprises the same nucleic acid sequences.

17. The method of claim 1, wherein the first attachment moiety and the second attachment moieties are click moieties.

18. The method of claim 1, further comprising:
(d) modifying the polypeptide fragments by adding exogenous moieties at amino acids of the polypeptide fragments as the first attachment moieties.

19. The method of claim 1, wherein the first attachment moieties are positioned at lysine amino acids of the polypeptide.

* * * * *